US008653046B2

(12) United States Patent
Fussenegger et al.

(10) Patent No.: US 8,653,046 B2
(45) Date of Patent: Feb. 18, 2014

(54) CONTROLLING TRANSGENE EXPRESSION ACROSS THE SKIN

(75) Inventors: Martin Fussenegger, Mägenwil (CH); Marc Gitzinger, Binningen (CH)

(73) Assignee: ETH Zurich, Zurich (CH)

( * ) Notice: Subject to any disclaimer, the term of this patent is extended or adjusted under 35 U.S.C. 154(b) by 0 days.

(21) Appl. No.: 13/263,149

(22) PCT Filed: Apr. 1, 2010

(86) PCT No.: PCT/EP2010/002103
§ 371 (c)(1),
(2), (4) Date: Oct. 6, 2011

(87) PCT Pub. No.: WO2010/115583
PCT Pub. Date: Oct. 14, 2010

(65) Prior Publication Data
US 2012/0029074 A1    Feb. 2, 2012

(30) Foreign Application Priority Data
Apr. 9, 2009  (EP) .................................... 09005216

(51) Int. Cl.
*C12N 15/00*    (2006.01)
*C12N 15/06*    (2006.01)

(52) U.S. Cl.
USPC ........................................ 514/44 R; 435/455

(58) Field of Classification Search
USPC ....................................................... 514/44 R
See application file for complete search history.

(56) References Cited

FOREIGN PATENT DOCUMENTS

WO          99/25856      5/1999
WO      WO 9925856 A  *  5/1999  ............. C12N 15/85

OTHER PUBLICATIONS

Teran et al, J Biol Chem, 2006, 281:7102-7109.*
Rezk et al, Biochemical and Biophysical Research Communications, 2002, 295:9-13.*
Auner et al, Journal of Controlled Release, 2003, 89:321-328.*
Niidome and Huang, Gene Therapy, 2002, 9:1647-1652.*
Gao et al, The AAPS Journal, 2007, 9:E92-E104.*
Bartek et al, The Journal of Investigative Dermatology, 1972, 58:114-123.*
Cascalho et al, J Am Soc Nephrol, 2004, 15:1106-1112.*
International Search Report issued Aug. 2, 2010 in International (PCT) Application No. PCT/EP2010/002103 along with the Written Opinion.
W. Teran et al., "Effector-Repressor Interactions, Binding of a Single Effector Molecule to the Operator-Bound TtgR Homodimer Mediates Derepression", The Journal of Biological Chemistry, vol. 281, No. 11, pp. 7102-7109, Mar. 17, 2006.
B. G. Auner et al., "Infleuence of Phloretin and 6-Ketocholestanol on the Skin Permeation of Sodium-Fluorescein", Journal of Controlled Release, vol. 89, No. 2, pp. 321-328, Apr. 29, 2003.
Y. Alguel et al., "Crystal Structures of Multidrug Binding Protein TtgR in Complex with Antibiotics and Plant Antimicrobials", Journal of Molecular Biology, vol. 369, No. 3, pp. 829-840, May 11, 2007.
W. Teran et al., "Complexity in Efflux Pump Control: Cross-Regulation by the Paralogues TtgV and TtgT", Molecular Microbiology, vol. 66, No. 6, pp. 1416-1428, 2007.

* cited by examiner

*Primary Examiner* — Valarie Bertoglio
*Assistant Examiner* — Chi-Feng Hsu
(74) *Attorney, Agent, or Firm* — Wenderoth, Lind & Ponack, L.L.P.

(57) ABSTRACT

The invention relates to the use of a skin permeating compound such as phloretin for controlling transgene expression under control of the *Pseudomonas putida* DOT-T1E-derived bacterial repressor TtgR, to a vector comprising the genetic code for the repressor TtgR fused to a transactivation or a transrepressor domain, to a vector comprising a TtgR-specific operator sequence ($O_{TtgR}$), a promoter and a polynucleotide coding for an endogenous or exogenous protein, and to a mammalian cell transiently or constitutively transfected with the mentioned vectors, and to mammals comprising such cells in nano- or microcontainers.

6 Claims, 12 Drawing Sheets

A

B

CONTROLLING TRANSGENE EXPRESSION ACROSS THE SKIN

This application is a U.S. national stage of International Application No. PCT/EP2010/002103 filed Apr. 1, 2010.

FIELD OF THE INVENTION

The invention relates to the use of a skin permeating compound for controlling transgene expression, and corresponding vectors and cells comprising such vectors enabling such transgene expression.

BACKGROUND OF THE INVENTION

Synthetic mammalian expression circuits which enable reversible and adjustable transgene expression have been essential for recent advances in functional genomic research, drug discovery, manufacturing of difficult-to-produce protein therapeutics, the design of synthetic gene networks replicas reaching the complexity of electronic circuits and gene therapy applications.

To date, a multitude of heterologous transgene expression systems, for use in mammalian cells and transgenic animals, have been described (Weber W., Fussenegger M., 2007, Curr Opin Biotechnol 18(5):399-410). The prevailing design consists of a heterologous small molecule-responsive transactivator engineered by fusing a prokaryotic repressor to an eukaryotic transactivation domain and a transactivator-specific promoter containing the matching prokaryotic operator linked to a minimal eukaryotic promoter. Inducer-triggered modulation of the transactivator's affinity to its cognate promoter results in adjustable and reversible transcription control of the specific target gene. In recent years, a panoply of such heterologous transcription control modalities have been developed which are responsive to a variety of inducer molecules such as antibiotics, steroid hormones and their analogs, quorum-sensing molecules, immunosuppressive and anti-diabetic drugs, biotin, L-arginine as well as volatile acetaldehyde (WO2005/021766). Apart from gaseous acetaldehyde which can simply be inhaled, all other inducers need to be either taken up orally or be administered by injection in any future gene therapy application. Transdermal and topical delivery of inducer molecules, which would provide advantages over conventional injection-based or oral administration such as convenience, improved patient compliance and elimination of hepatic first-pass effect, have not yet been developed.

Phloretin, which is a natural plant defense metabolite with antibacterial activity (Teran W., Krell T., Ramos J. L., Gallegos M. T., 2006, J Biol Chem 281(11):7102-7109), occurring in the root bark of apple trees as well as in apples, has been studied as a possible penetration enhancer for skin-based drug delivery, attenuates inflammation by antagonizing prostaglandins, protects the skin from UV light-induced photodamage and is evaluated as a chemopreventive agent for cancer treatment. Since the plant rhizosphere is one of the natural habitats of Pseudomonas putida (strain DOT-T1E), this prokaryote has evolved the RND family transporter TtgABC with multidrug recognition properties which is controlled by its cognate repressor TtgR binding to a specific operator, ($O_{TtgR}$) in the TtgR promoter ($P_{TtgR}$). Phloretin has been shown to bind to the TtgR-operator complex at a stoichiometric ratio of one effector molecule per dimer of TtgR and to release TtgR from $O_{TtgR}$ which results in induction of TtgABC production and effective pump-mediated efflux of the flavonoid from P. putida (Teran W. et al., loc. cit.).

SUMMARY OF THE INVENTION

The invention relates to the use of a skin permeating compound for controlling transgene expression, in particular transgene expression under control of the Pseudomonas putida DOT-T1E-derived bacterial repressor TtgR. A skin permeating compound to be used in the invention is, for example, a flavonoid or chalcone, e.g. phloridzin, phloretin, and the like, butylparaben, or derivatives thereof, in particular phloretin.

The invention further relates to a vector comprising the genetic code of the Pseudomonas putida DOT-T1E-derived bacterial repressor TtgR fused to a transactivation or a transrepressor domain, in particular a vector comprising the genetic code for TtgR and the vp16 transactivation domain of Herpes simplex virus and the constitutive simian virus 40 promoter ($P_{SV40}$) such that the transactivator $TtgA_1$ resulting from the fusion of the proteins TtgR with VP16 is under control of $P_{SV40}$.

The invention also relates to the corresponding encoded transactivator and transrepressor proteins, e.g. the protein $TtgA_1$.

Furthermore the invention relates to a vector comprising a TtgR-specific operator sequence ($O_{TtgR}$), a promoter and a polynucleotide coding for an endogenous or exogenous protein, for example the minimal human cytomegalovirus immediate early promoter ($P_{hCMVmin}$), and a vector comprising both components, i.e. the genetic code for the TtgR-protein fused to a transactivation domain or a transrepressor domain, a polynucleotide coding for an endogenous or, preferably, exogenous protein, a TtgR-specific operator sequence ($O_{TtgR}$) and a promoter.

The invention also relates to a mammalian cell transiently or constitutively transfected with the mentioned vectors, such mammalian cells in nano- or micro-containers, and mammals comprising such a mammalian cell.

CHO-K1 engineered for constitutive SEAP expression are cultivated in culture medium supplemented with different phloretin concentrations (0-100 μM) and SEAP production (bars) as well as maximum cell density are assessed after 48 h (line). Abbreviations: C.D.: Cell Density ($10^6$/mL); Phl.: Phloretin (μM)

Figure 2:
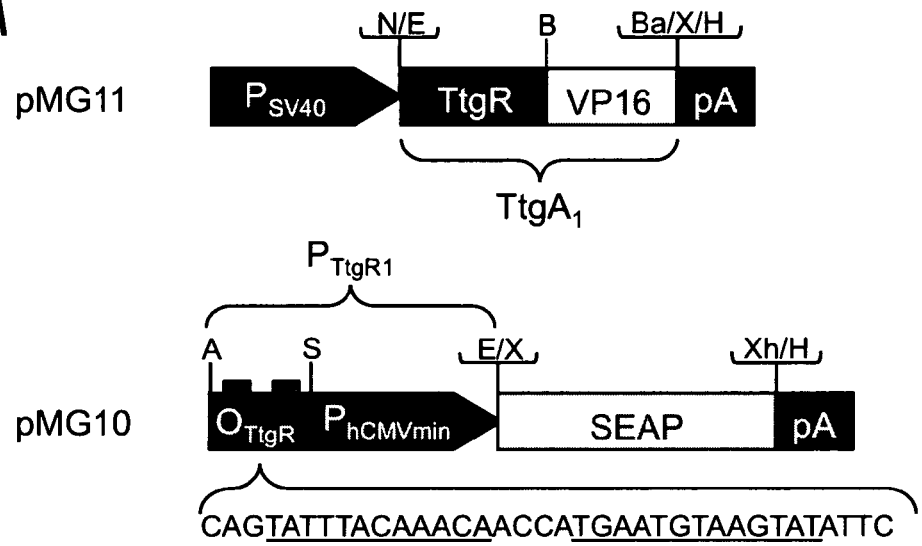
Figure 2:
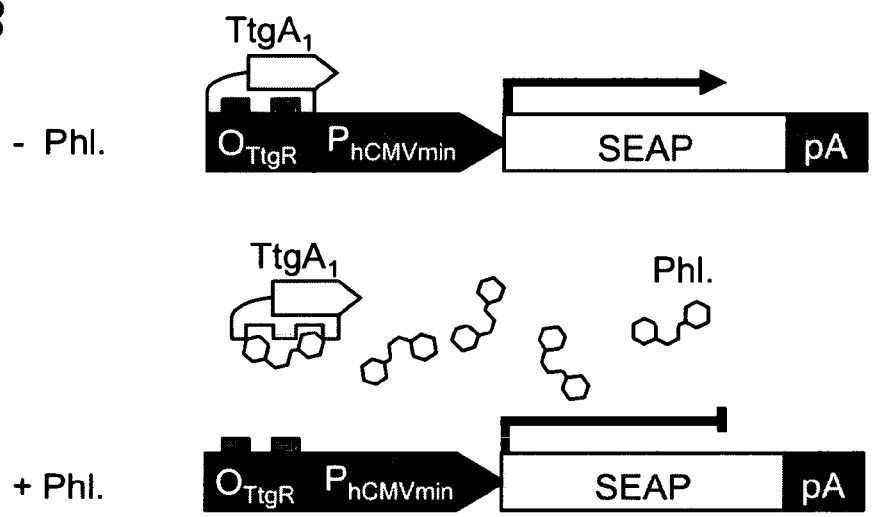
Figure 2:
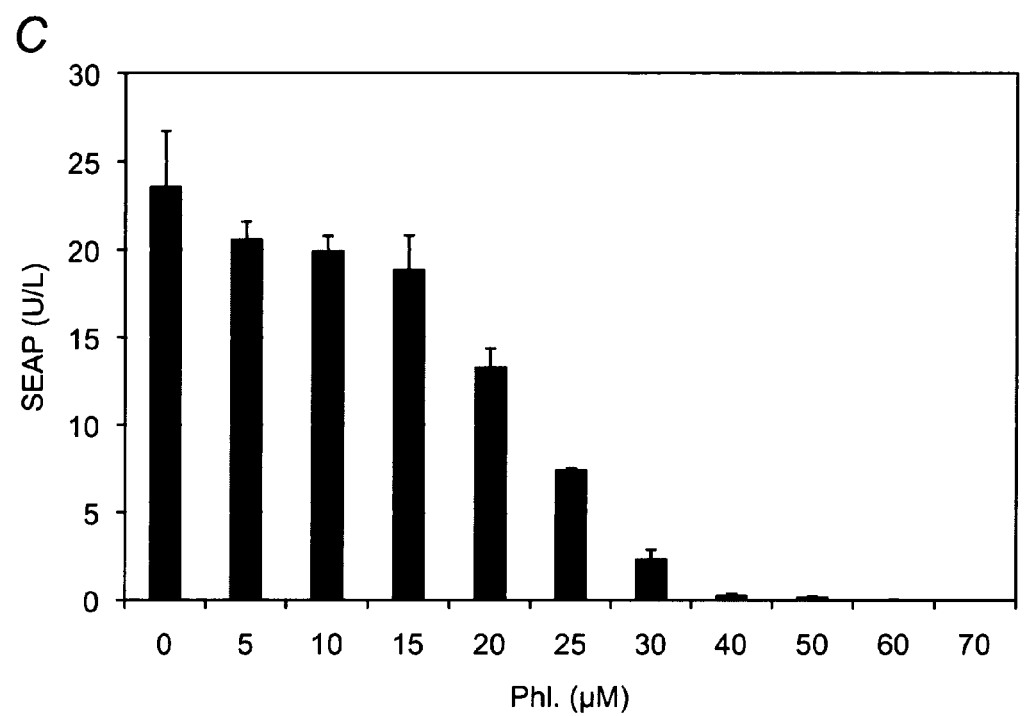

FIG. 2. Design and functionality of phloretin-adjustable control element (PEACE).

(A) Expression vectors. The genetic code for the Pseudomonas putida DOT-T1E-derived bacterial repressor TtgR-protein is fused to the VP16 transactivation domain of Herpes simplex virus and the resulting transactivator $TtgA_1$ (TtgR-VP16) is cloned under control of the constitutive simian virus 40 promoter ($P_{SV40}$) (pMG11). The phloretin-responsive promoter ($P_{TtgR1}$: $O_{TtgR}$-$P_{hCMVmin}$) contains a TtgR-specific operator sequence ($O_{TtgR}$, TtgR binding sites underlined), which is located 5' of a minimal human cytomegalovirus immediate early promoter ($P_{hCMVmin}$) and is set to drive expression of the human placental secreted alkaline phosphatase (SEAP) (pMG10). Selected restriction sites: A, AatII; B, BssHII; Ba, BamHI; E, EcoRI; H, HindIII; N, NotI; S, SbfI; X, XbaI; Xh, XhoI.

(B) Schematic representation of PEACE functionality. In the absence of phloretin, $TtgA_1$ binds to its cognate operator site and initiates $P_{TtgR1}$-driven SEAP expression. Addition of phloretin releases $TtgA_1$ from $P_{TtgR1}$, which switches off SEAP expression.

(C) SEAP expression profiles of CHO-K1 transiently transfected with pMG11 ($P_{SV40}$-$TtgA_1$-pA) and pMG10 ($P_{TtgR1}$-SEAP-pA) and cultivated for 48 h in the presence of different phloretin concentrations (0-70 μM).

Abbreviations: Phl.: Phloretin (μM)

Figure 3:
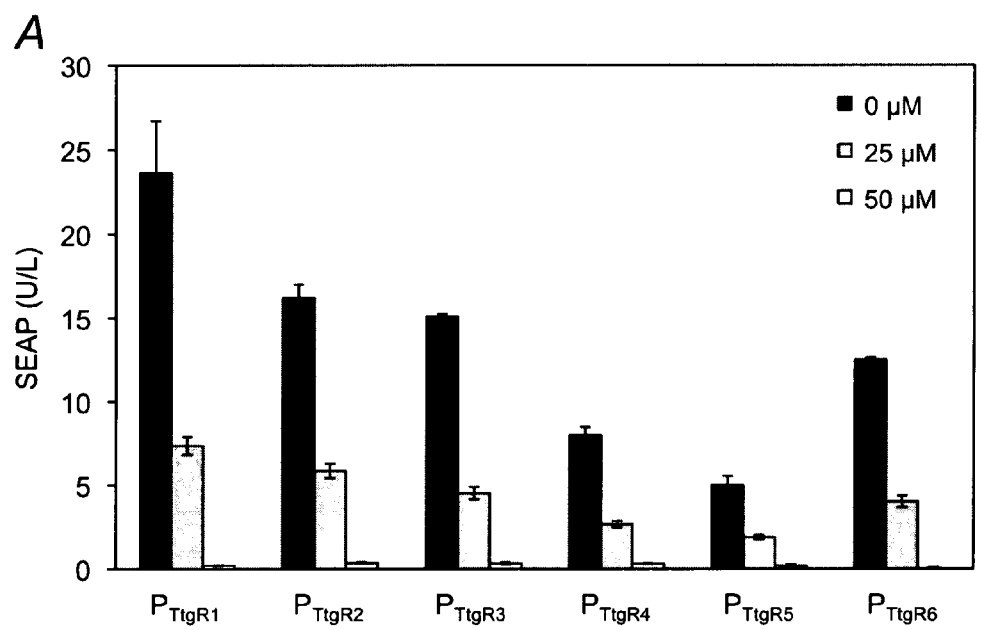
Figure 3:
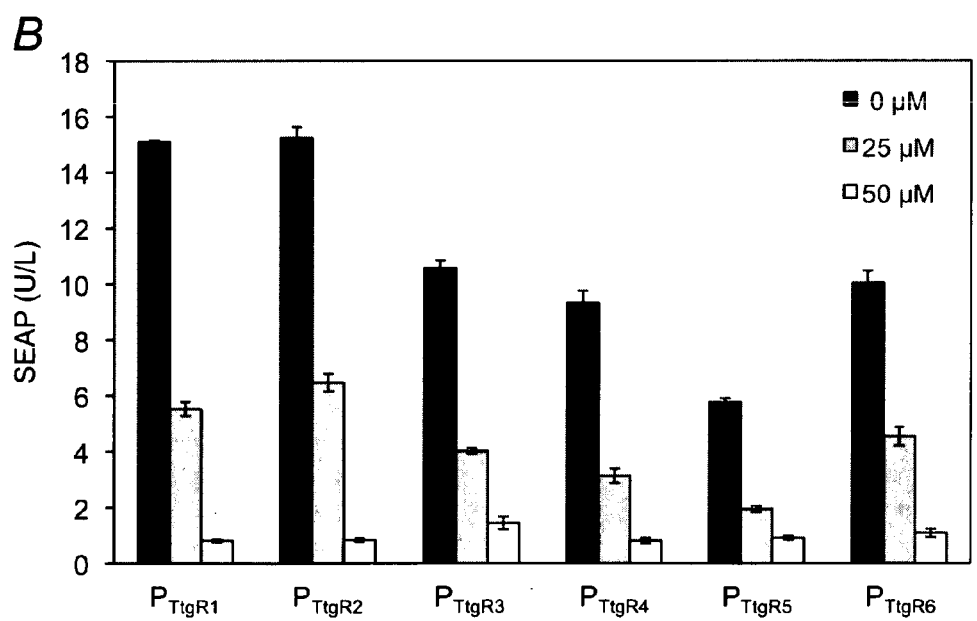
Figure 3:
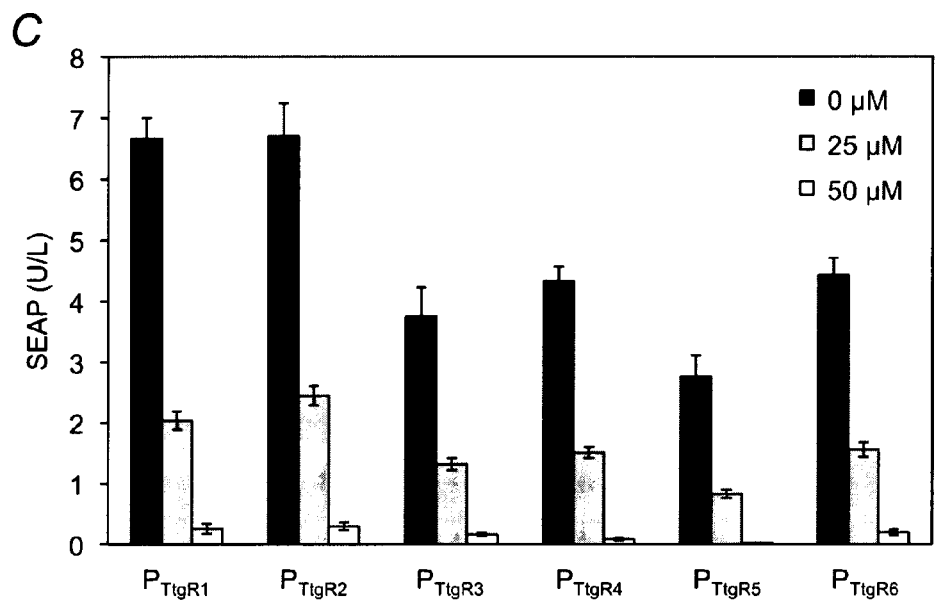

FIG. 3. Design and combinatorial characterization of different PEACE transactivator and promoter configurations.

PEACE transactivators harboring different transactivation domains (A, $TtgA_1$, VP16; pMG11) (B, $TtgA_2$, p65; pMG18) (C, $TtgA_3$, E2F4; pMG19) are co-transfected with SEAP-driving PEACE promoter variants containing 0 ($P_{TtgR1}$; pMG10), 2 ($P_{TtgR2}$; pMG20), 4 ($P_{TtgR3}$; pMG21), 6 ($P_{TtgR4}$; pMG22), 8 ($P_{TtgR5}$; pMG23) and 10 ($P_{TtgR6}$; pMG24) base pair linkers between the TtgR operator and the minimal promoter into CHO-K1, and SEAP expression is profiled after 48 h of cultivation in medium supplemented with different phloretin concentrations.

Figure 4:
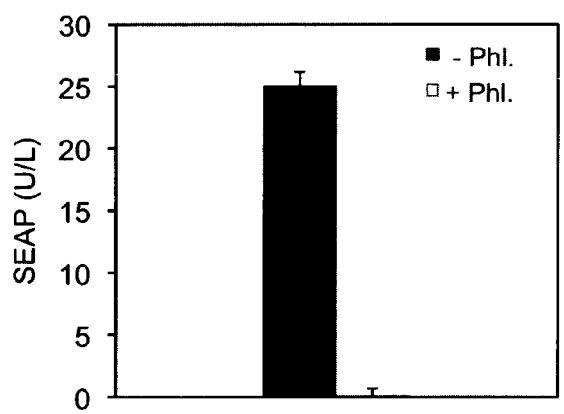

FIG. 4. Autoregulated PEACE-controlled SEAP expression in CHO-K1.

pMG13 encoding a $P_{TtgR1}$-driven dicistronic expression unit harboring SEAP in the first and $TtgA_1$ in the second cistron is transfected into CHO-K1 and SEAP expression is assessed 48 h after cultivation in the presence (50 μM) and absence of phloretin.

Abbreviations: Phl.: Phloretin

Figure 5:
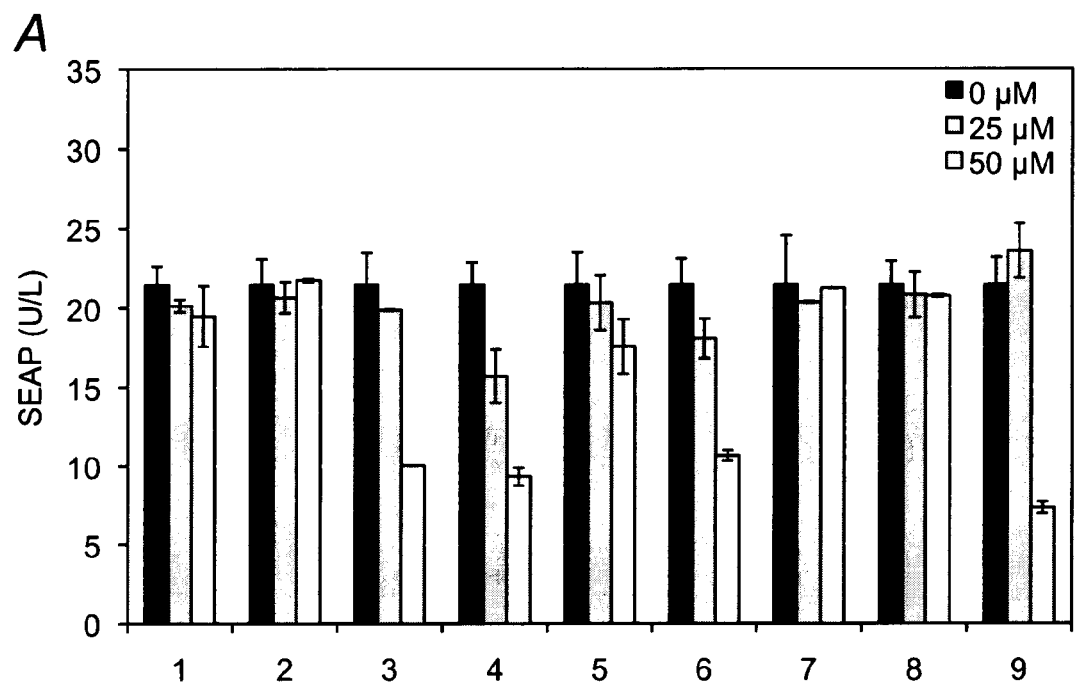
Figure 5:
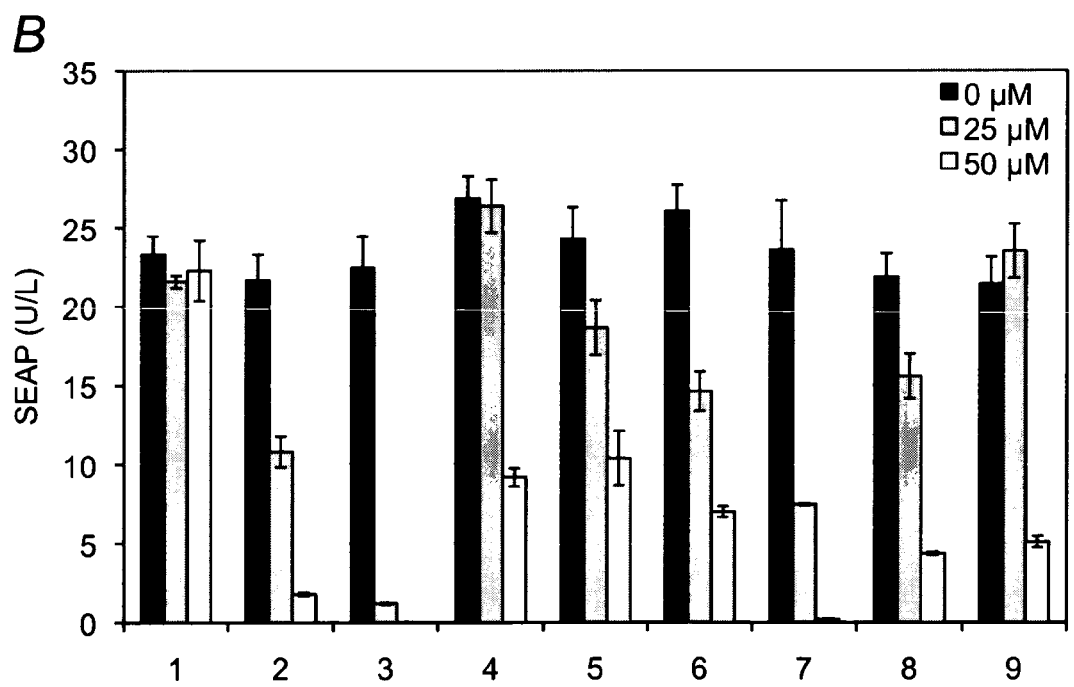

FIG. 5. PEACE responsiveness to different flavonoids.

(A) Toxicity of flavonoids. CHO-K1 are transiently transfected with pSEAP2-Control, and cultivated in medium supplemented with different flavonoids (0, 25, 50 μM). SEAP levels are scored after 48 h.

(B) CHO-K1 cells transiently expressing all PEACE components (pMG10 and pMG11) are cultivated in the presence of different flavonoids and SEAP expression is profiled after 48 h Abbreviations: 1: Berberine; 2: Butylparaben; 3: Genistein; 4: Luteolin; 5: β-Naphtol; 6:

Naringenin; 7: Phloretin; 8: Phloridzin; 9: Quercetin

Figure 6:
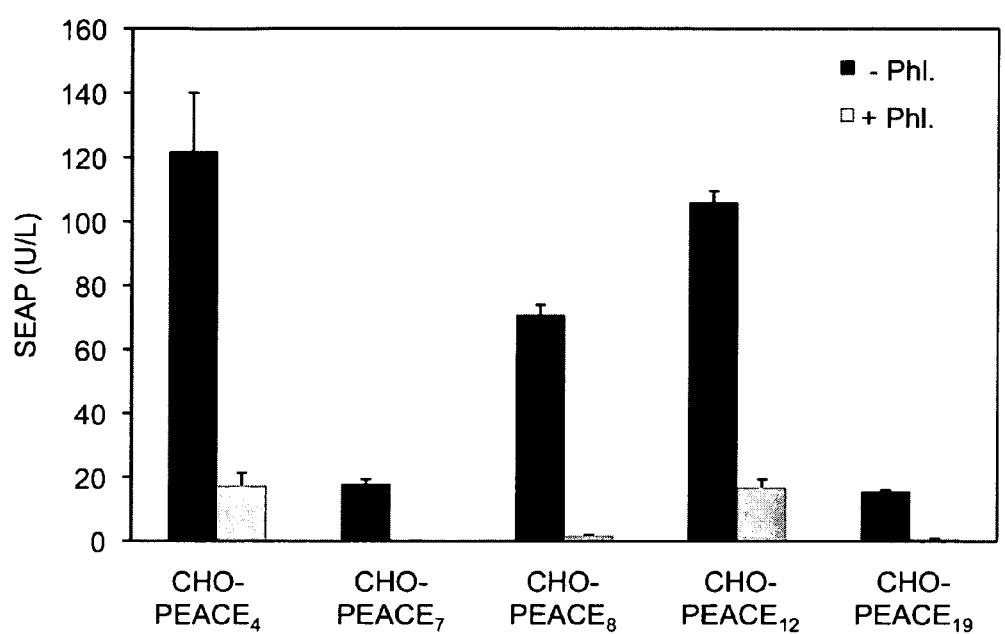

FIG. 6. Design and characterization of stable CHO-PEACE cell lines transgenic for phloretin-responsive SEAP expression.

CHO-K1 is stably co-transfected with pMG11 ($P_{SV40}$-$TtgA_1$-pA) and pMG10 ($P_{TtgR1}$-SEAP-pA) and individual clones are assessed for phloretin-modulated SEAP expression after a cultivation period of 48 h.

Abbreviations: Phl.: Phloretin

Figure 7:
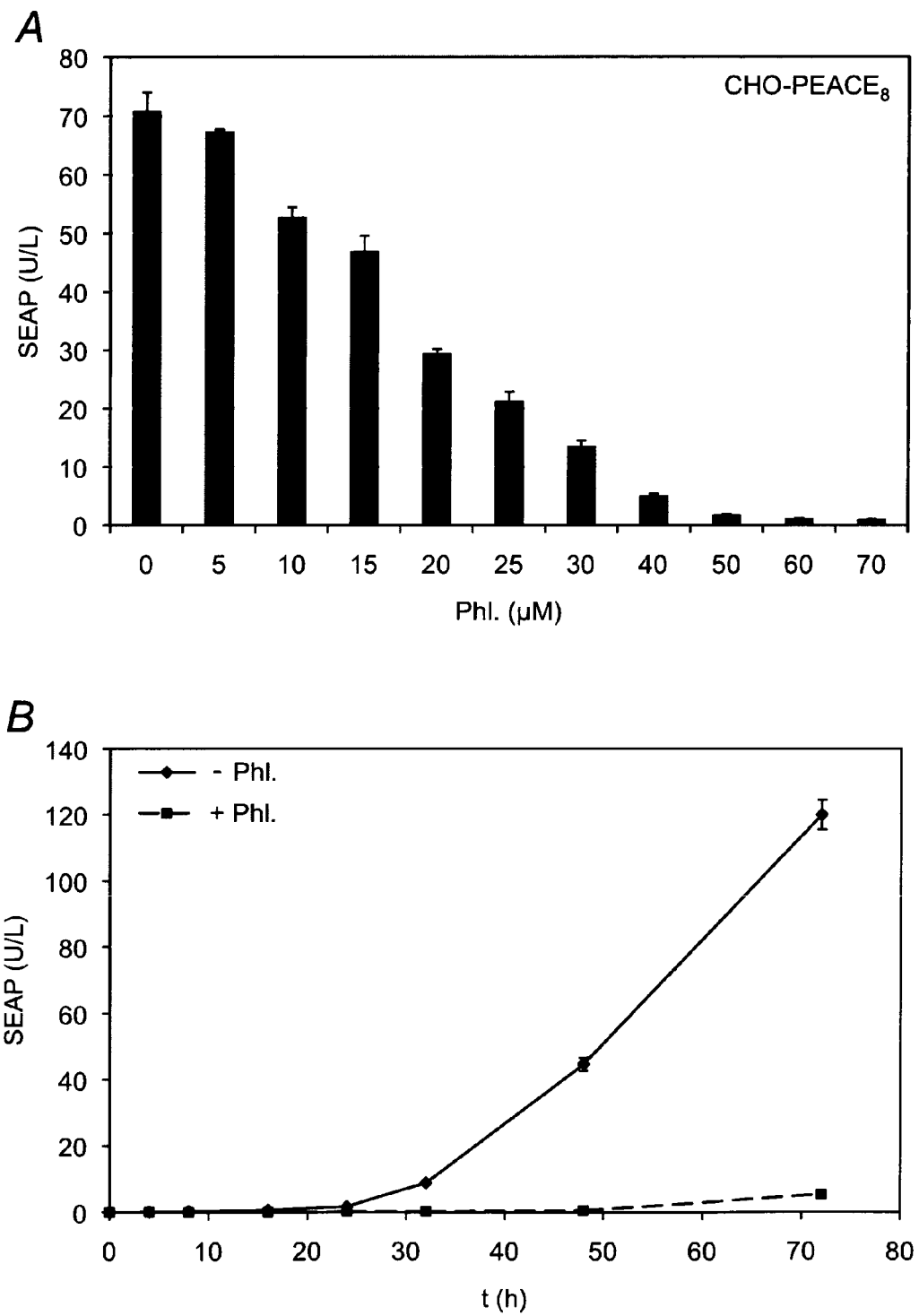
Figure 7:
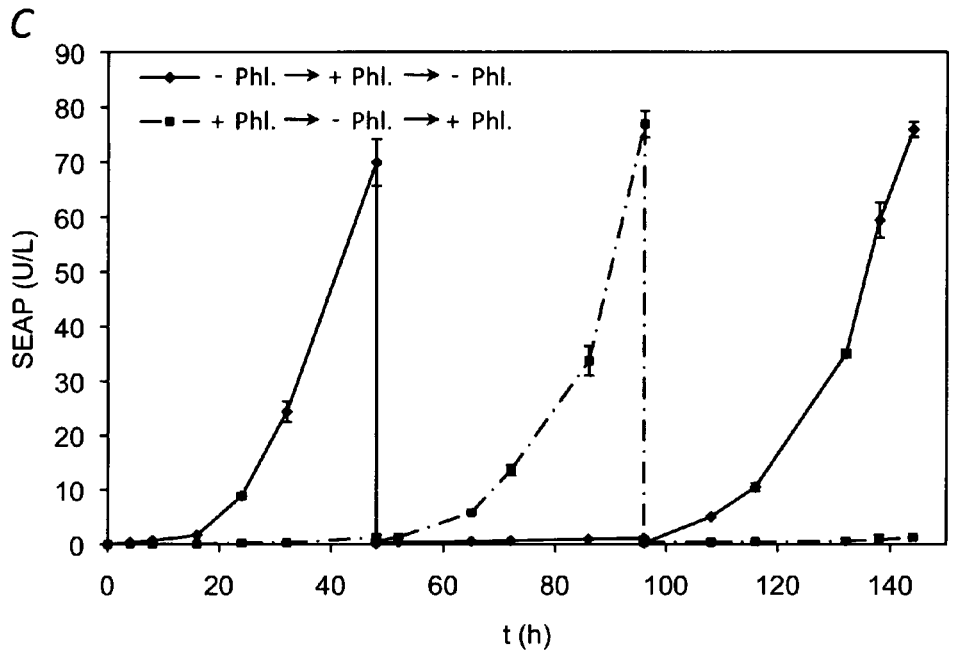

FIG. 7. Design and characterization of the stable CHO-$PEACE_8$ cell line transgenic for phloretin-responsive SEAP expression.

(A) Dose-response profile of CHO-$PEACE_8$.

(B) SEAP expression kinetics of CHO-$PEACE_8$ cultivated for 72 h in the presence and absence of 50 μM phloretin.

(C) Reversibility of CHO-$PEACE_8$-based SEAP production. $2 \times 10^5$ CHO-$PEACE_8$ were cultivated for 144 h in the presence or absence of 50 μM phloretin. Every 48 h the cell density is readjusted to $2 \times 10^5$ and the phloretin status of the culture is reversed.

Abbreviations: Phl.: Phloretin (μM); t: Time (h).

Figure 8:
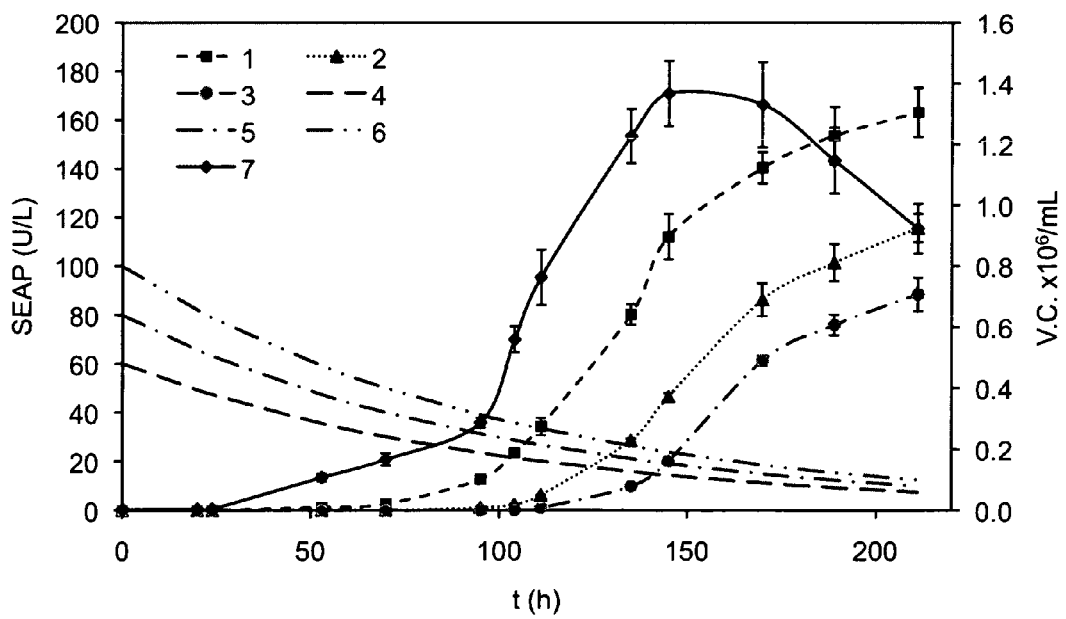

FIG. 8. Automatically programmed product gene expression in bioreactors using well-defined phloretin degradation profiles.

$2 \times 10^3$ cells/mL CHO-$PEACE_8$ are cultivated in a bioreactor containing 1 L culture medium supplemented with either 60, 80 or 100 μM phloretin and SEAP production is profiled for 211 h. Owing to a defined phloretin degradation profile in culture and a precise induction threshold of 40 μM phloretin, the onset of SEAP production can be programmed to occur at a very precise point in time by defining the cell density and the phloretin concentration at production start.

Abbreviations: 1: Phloretin (60 μM); 2: Phloretin (80 μM); 3: Phloretin (100 μM); 4: Phloretin degradation (60 μM); 5: Phloretin degradation (80 μM); 6: Phloretin degradation (100 μM); 7: Cell Number; V.C.: Viable Cells ($10^6$/mL)

Figure 9:
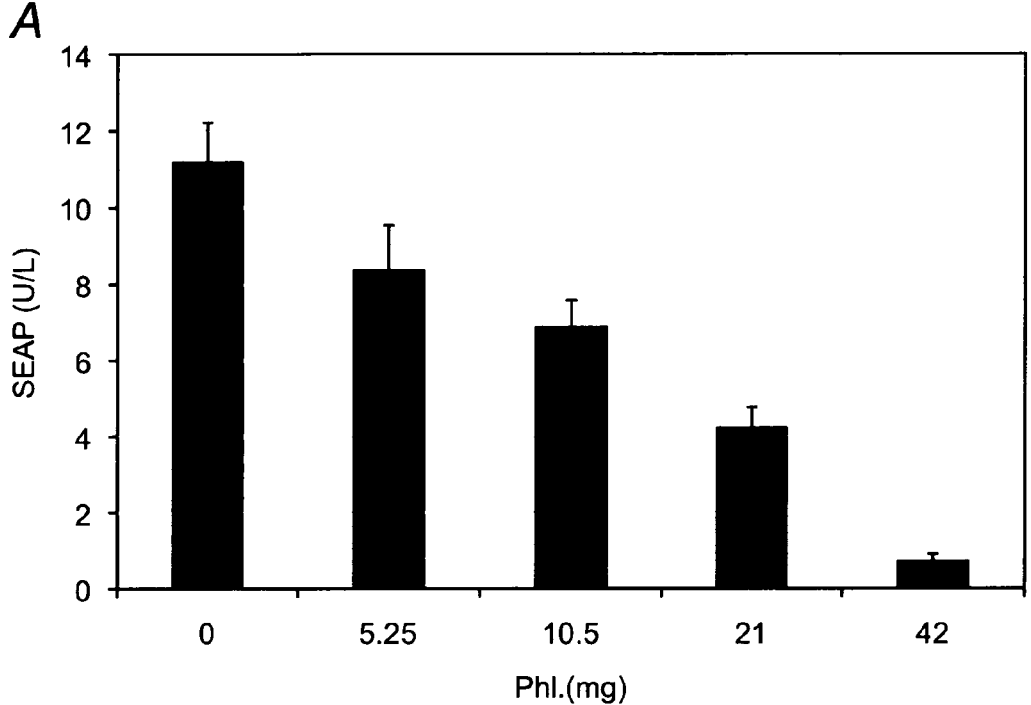
Figure 9:
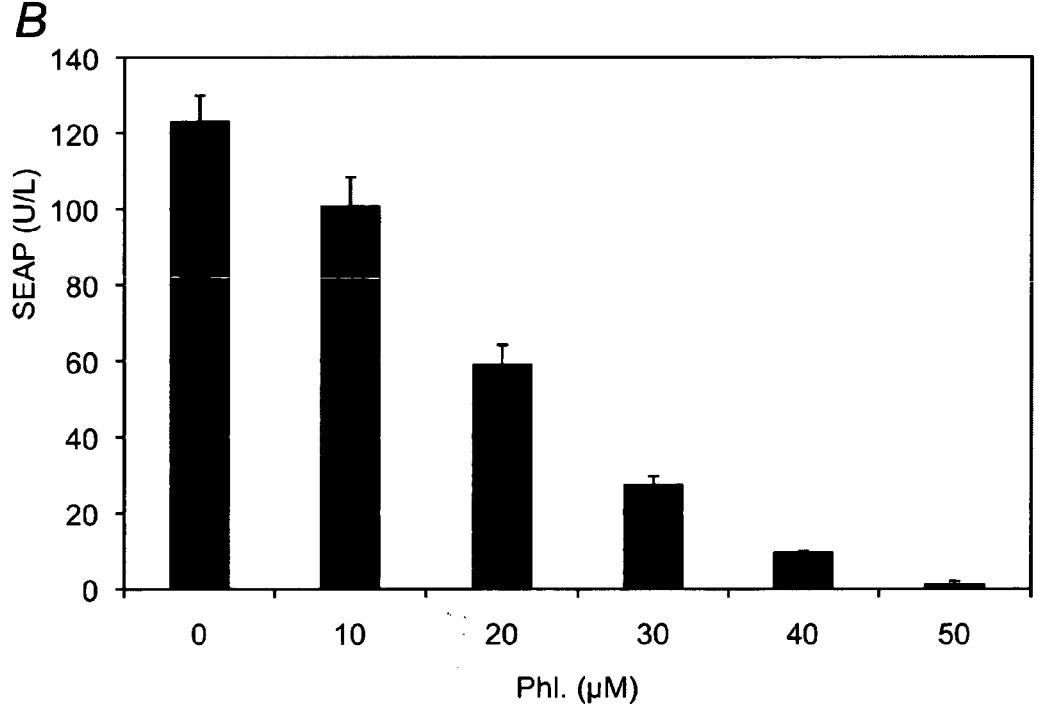

FIG. 9. PEACE-controlled transgene expression in mice.

(A) Microencapsulated CHO-$PEACE_8$ are implanted subcutaneously into female OF1 mice ($2 \times 10^6$ cells/mouse). 200 μL of a cream containing different amounts of phloretin (0, 5.25, 10.5, 21 and 42 mg) is applied to a shaved skin area near the implant site. SEAP serum levels are quantified 72 h post implantation.

(B) SEAP expression profiles of the microencapsulated CHO-$PEACE_8$ implant batch cultivated in vitro for 72 h at different phloretin concentrations.

Abbreviations: Phl.: Phloretin (μM)

Figure 10:
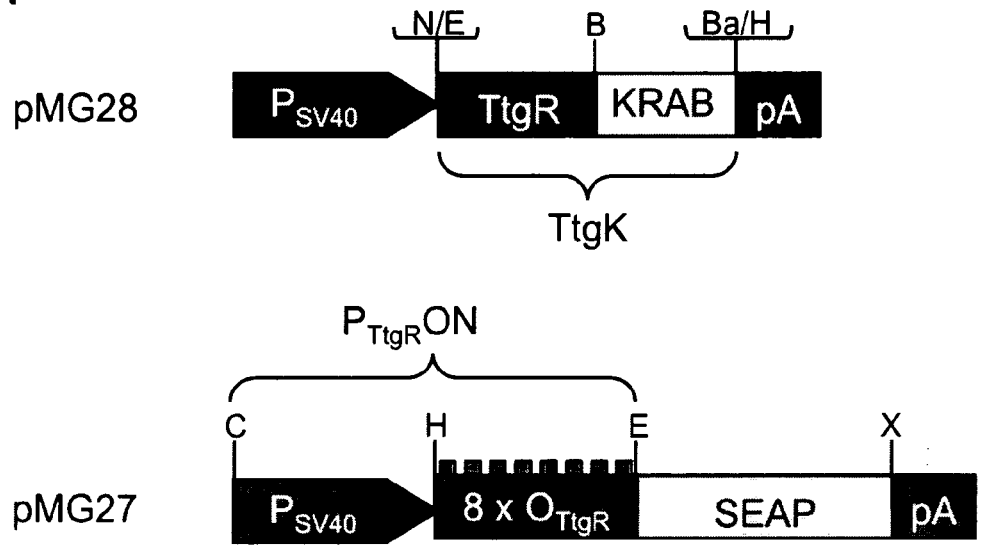
Figure 10:
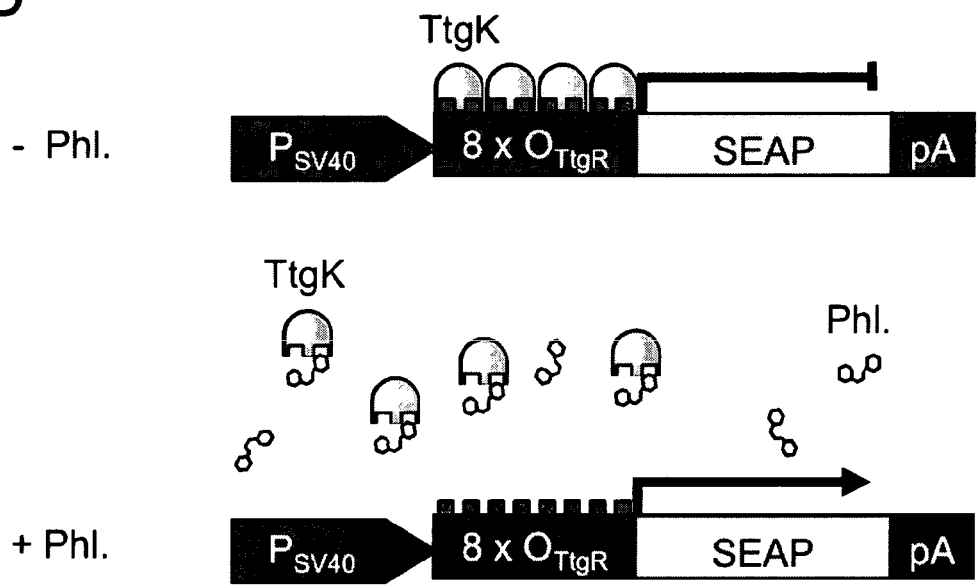
Figure 10:
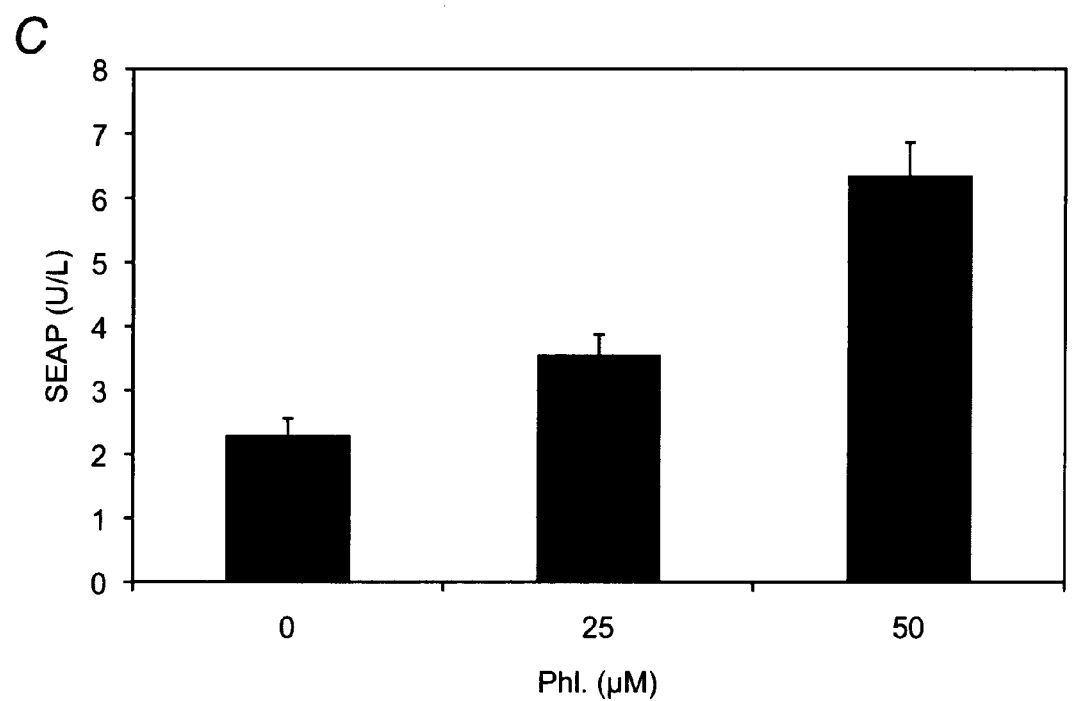

FIG. 10. Design and functionality of a phloretin-adjustable control element (PEACE-ON) for positive regulation.

(A) Expression vectors. The genetic code for the *Pseudomonas putida* DOT-T1E-derived bacterial repressor protein TtgR is fused to the KRAB transrepression domain of human Kruppel-associated box-protein and the resulting transrepressor protein TtgK (TtgR-KRAB) is cloned under control of the constitutive simian virus 40 promoter ($P_{SV40}$) (pMG28). The phloretin-responsive promoter ($P_{TtgR}ON$; $P_{SV40}$-$8 \times O_{TtgR}$) contains eight TtgK-specific, operator sequences ($8 \times O_{TtgR}$), which are located 3' of the constitutive $P_{SV40}$ and is set to drive expression of the human placental secreted alkaline phosphatase (SEAP) (pMG27). Selected restriction sites: B, BssHII; Ba, BamHI; C, ClaI; E, EcoRI; H, HindIII; N, NotI; X, XbaI;

B) Schematic representation of PEACE-ON functionality. In the absence of phloretin, TtgK binds to its cognate operator site and inhibits $P_{TtgR}ON$-driven SEAP expression. Addition of phloretin releases TtgK, from $P_{TtgR}ON$, which switches on SEAP expression.

(C) SEAP expression profiles of CHO-K1 transiently transfected with pMG28 ($P_{SV40}$-TtgK-pA) and pMG27 ($P_{TtgR}ON$-SEAP-pA) and cultivated for 48 h in the presence of different phloretin concentrations (0-50 μM).

DETAILED DESCRIPTION OF THE INVENTION

Capitalizing on the phloretin-responsive TtgR-$O_{TtgR}$ interaction of *P. putida* DOT-T1E a synthetic mammalian phloretin-adjustable control element (PEACE) is assembled which is able to reversibly fine-tune transgene expression of cell implants in mice using a phloretin-containing skin lotion and can be used to program production cell lines for automatic product gene expression in standard bioreactor operation.

Phloretin is 3-[4-hydroxyphenyl]-1-[2,4,6-trihydroxyphenyl]-1-propanone) of the formula

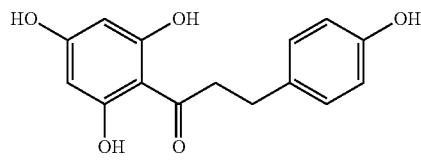 [SMILES: O=C(CCc1ccc(O)cc1)c1c(O)cc(O)cc1O]

The invention relates to the use of a skin permeating compound for controlling transgene expression, in particular transgene expression under control of the *Pseudomonas putida* DOT-T1E-derived bacterial repressor protein TtgR. A skin permeating compound to be used in the invention is, for example, a flavonoid or chalcone, e.g. phloridzin, phloretin, and the like, butylparaben, or derivatives thereof, in particular phloretin.

A flavonoid includes isoflavonoids and neoflavonoids and is a natural product derived from 2-phenylchromen-4-one (flavone), 3-phenylchromen-4-one (isoflavone), and 4-phenyl-coumarin (neoflavone). A chalcone is closely related to the flavanoids and represents an open chain analog derived from o-hydroxyphenyl phenylvinyl ketone. Derivations include reduction of the 2(3) carbon-carbon double bond of flavone to give flavanones (the ring-closed isomer of a chalcone) or further reduction (and ring cleavage) to give o-(3-phenyl-propanoyl)phenol (dihydrochalcone), reduction of the keto group to give flavanols or further reduction to a $CH_2$ group, and hydroxylation (including multiple hydroxylations) at various positions, and also salts, methyl ether and glycosidic ether derivatives, and acetates and gallic acid esters of such hydroxylated compounds.

Butylparaben is butyl 4-hydroxybenzoate. Phloridzin is 1-[2,4-dihydroxy-6-[(2S,3R,4S,5S,6R)-3,4,5-trihydroxy-6-(hydroxymethypoxan-2-yl]oxyphenyl]-3-(4-hydroxyphenyl)propan-1-one, i.e. a flavonoid glycoside.

Derivatives of phloretin are, for example, salts with cations, ethers and esters. Particular salts are mono-, di-, tri- or tetra-valent salts, for example alkali salts, such as lithium, sodium or potassium salts, earth alkali salts, for example calcium or magnesium salts, aluminium salts, transition metal salts, for example ferrous or ferric salts, ammonium salts, for example ammonium, methylammonium, dimethylammonium, trimethylammonium or tetramethylammonium salts, alkyltrimethylammonium salts, wherein alkyl is, for example $C_2$-$C_{20}$-alkyl, in particular $C_6$-$C_{20}$-alkyl, such as $C_{12}$, $C_{14}$, $C_{16}$ or $C_{18}$-alkyl, hydroxyethyl-ammonium, di(hydroxyethyl)ammonium, or tri(hydroxyethyl)ammonium salts.

Particular ethers are mono-, di-, tri- or tetra-ethers, for example methyl or ethyl ethers, in particular tri- and tetramethyl ethers, and glycosides. Particular esters are mono-, di-, tri- or tetra-esters, for example acetyl esters, in particular tri- and tetraacetyl esters, and gallic acid esters.

Derivatives of butylparaben are likewise salts, e.g. the sodium salt, ethers, e.g. butyl 4-methoxybenzoate, or esters, e.g. butyl 4-acetoxybenzoate.

Derivatives of phloridzin are likewise salts, e.g. sodium salts, ethers, e.g. methyl or ethyl ethers, or esters, e.g. acetates.

Flavonoids or chalcones such as phloretin are polyphenols widely distributed in the plant kingdom and are present in fruits and vegetables regularly consumed by humans. Recent findings that phloretin and some of its derivatives have potent anti-inflammatory, antioxidative and even some anti-cancer activities form the scientific basis for the common saying "an apple a day keeps the doctor away". Phloretin has also been successfully evaluated as a penetration enhancer for transdermal drug delivery (Auner B. G., Valenta C., Hadgraft J., 2003, *J Control Release* 89(2):321-328; Valenta C., Cladera J., O'Shea P., Hadgraft J., 2001, *J Pharm Sci* 90(4):485-492) and as skin protectant reducing oxidative stress resulting from external insults, such as UV irradiation which triggers skin cancer and photo aging. Recent studies in rodents have confirmed that dermal administration of phloretin will systemically spread in the animal (Auner et al., loc. cit.) and that phloretin has a rather short half-life in vivo. All of the aforementioned characteristics corroborate phloretin to be a non-toxic natural compound with high metabolic turnover which is ideal for reversible transdermal induction of therapeutic transgenes. Transdermal and topical delivery of drugs and regulating molecules provide advantages over conventional oral or injection-based administrations, such as convenience, improved patient compliance and elimination of hepatic first-pass effect. However, most molecules are not applicable to dermal administration due to the excellent barrier properties of the skin which requires penetrating molecules to pass the stratum corneum with its compact keratinized cell layers and the viable epidermis before reaching the papillary dermis and crossing the capillary walls into systemic circulation. Phloretin-containing skin lotions put on the skin of mice containing cell implants harboring a synthetic phloretin-responsive expression circuit are able to precisely fine-tune target gene expression in the animal. This pioneering transdermal transcription control system enables precise patient-controlled dosing of protein pharmaceuticals that are produced in situ by cell implants contained in clinically licensed devices. Besides this gene therapy-focused in vivo scope of phloretin-responsive transgene expression the system shows excellent regulation performance including adjustability and reversibility in vitro. Owing to its short half-life in culture, phloretin-responsive production cultures grown in bioreactors can be preprogrammed for timely production initiation by inoculation with excessive phloretin concentrations. While the production cell cultures grow and phloretin levels decrease following precise kinetics, production will be initiated at a defined point in time which is a function of the inoculum and the initial phloretin concentration. Such a time-delayed production concept is particularly valuable for difficult-to-express protein therapeutics like those which impair growth or are cytotoxic. The fact that phloretin is a natural fruit component regularly consumed by humans and licensed for use in skin lotions facilitates approval of such biopharmaceutical manufacturing protocols by governmental agencies.

Stability and Impact of Phloretin on Mammalian Cell Cultures.

Figure 1:
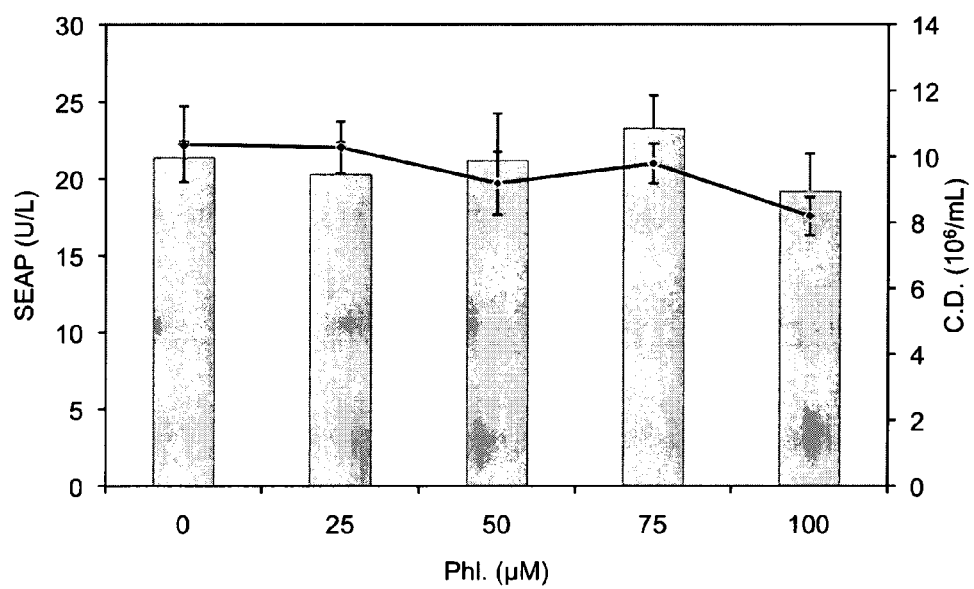
FIG. 1. Impact of phloretin on cell proliferation and protein production.

To evaluate the stability of phloretin in culture medium and assess its impact on mammalian cells, standard ChoMaster® HTS medium is supplemented with increasing concentrations of phloretin (0, 25, 50, 75, 100 µM), and this medium is incubated in the presence and absence of CHO-K1 engineered for constitutive SEAP expression (pSEAP2-Control; $P_{SV40}$-SEAP-pA, Clontech). The SEAP levels in samples taken from the cultures after 48 h indicate that phloretin has no negative impact on heterologous protein production which is a master indicator for metabolic integrity and viability. Parallel scoring of viable cell density confirms that the apple flavonoid does not compromise CHO-K1 proliferation up to 100 µM (FIG. 1). Phloretin levels determined over a period of 64 h in cell-free culture medium establish a functional half-live of 70 h for this flavonoid.

The invention relates to a vector comprising the genetic code of the *Pseudomonas putida* DOT-T1E-derived bacterial repressor TtgR fused to a transactivation domain or a transrepressor domain. Furthermore the invention relates to a vector comprising a TtgR-specific operator sequence ($O_{TtgR}$), a promoter and a polynucleotide coding for an endogenous or, preferably, exogenous protein.

Design of a Synthetic Mammalian Phloretin-Adjustable Control Element (PEACE).

Living in the plant rhizosphere, *Pseudomonas putida* DOT-T1E has evolved resistance to a variety of plant-derived antimicrobials, which is triggered by phloretin-induced release of TtgR protein from the operator ($O_{TtgR}$) of its target promoter and subsequent induction of a broadly specific TtgABC efflux pump (Teran W. et al., loc. cit.). By fusing TtgR (Teran W., et al., 2003, *Antimicrob Agents Chemother* 47(10):3067-3072) to the Herpes simplex-derived transactivation domain VP16 (Triezenberg S. J., Kingsbury R. C., McKnight S. L., 1988, *Genes Dev* 2(6):718-729) a synthetic mammalian transactivator ($TtgA_1$) has been created, which is able to bind and activate transcription from promoters ($P_{TtgR1}$) harboring $O_{TtgR}$ linked to a minimal human cytomegalovirus immediate early promoter ($P_{hCMVmin}$), in a phloretin-responsive manner (FIGS. 2A and B). Co-transfection of the constitutive $TtgA_1$ expression vector pMG11 ($P_{SV40}$-$TtgA_1$-pA) and pMG10 ($P_{TtgR1}$-SEAP-pA) encoding a $TtgA_1$-specific $P_{TtgR1}$-driven SEAP expression unit, results in high-level SEAP expression (23.6±3.1 U/L), which compares with an isogenic vector containing a constitutive $P_{SV40}$-driven SEAP expression cassette (pSEAP2-Control; 21.4±1.0 U/L). Addition of increasing concentrations of phloretin (0-70 µM) to a culture of pMG10- and pMG11-co-transfected CHO-K1 cells results in dose-dependent reduction of SEAP expression up to complete repression (FIG. 2C). These data indicate that PEACE-controlled transgene expression is adjustable and enables complete repression within a non-toxic phloretin concentration range.

In particular the invention relates to a vector comprising the genetic code for TtgR, the vp16 transactivation domain of Herpes simplex virus and the constitutive simian virus 40 promoter ($P_{SV40}$) such that the transactivator $TtgA_1$ resulting from the fusion of the proteins TtgR with VP16 is under control of $P_{SV40}$. Likewise the invention relates to a vector comprising the genetic code for TtgR fused to the p65 transactivation domain and the constitutive simian virus 40 promoter ($P_{SV40}$) such that the transactivator $TtgA_2$ resulting from the fusion of TtgR with p65 is under control of $P_{SV40}$, and to a vector comprising the genetic code for TtgR fused to the e2f4 transactivation domain and the constitutive simian virus 40 promoter ($P_{SV40}$) such that the transactivator $TtgA_3$ resulting from the fusion of TtgR with E2F4 is under control of $P_{SV40}$. Further transactivation domains considered are domains derived from or related to GAL4, CTF/NF1, AP2, ITF1, Oct1 and Sp1, and also those listed in U.S. Pat. No. 6,287,813.

Engineering and Validation of Different Phloretin-Dependent Transactivator Variants.

Three different transactivators are designed, harboring either the VP16 ($TtgA_1$; pMG11, TtgR-VP16) (Triezenberg S. J. et al., loc. cit.), the p65 ($TtgA_2$; pMG18, TtgR-p65) (Urlinger S., et al., 2000, *Gene* 247(1-2):103-110) or the human E2F4 ($TtgA_3$; pMG19, TtgR-E2F4) (Akagi K., Kanai M., Saya H., Kozu T., Berns A., 2001, *Nucleic Acids Res* 29(4):e23) transactivation domains. pMG11, pMG18 or pMG19 are co-transfected with pMG10 ($P_{TtgR1}$-SEAP-pA) into CHO-K1, HEK-293 as well as primary human fibroblasts and keratinocytes, and SEAP expression is profiled after 48 h of cultivation in the presence or absence of 50 µM phloretin. The maximum levels of transgene production vary significantly among different transactivators: $TtgA_1$ enables the highest transactivation in all cell lines, $TtgA_2$ shows the best performance in human primary cells and $TtgA_3$ activity is inferior in all situations (Table 1). All transactivators mediate similar basal expression levels when phloretin is present in the medium, but due to their cell-type specificity and graded maximum transcription-initiation capacities, the three transactivators offer a selection of defined expression windows.

TABLE 1

Combinatorial profiling of different PEACE transactivators and promoters in various cell types

| | SEAP Production (U/L) | | | | | |
|---|---|---|---|---|---|---|
| | pMG10/pMG11 | | pMG10/pMG18 | | pMG10/pMG19 | |
| phloretin 50 µM | − | + | − | + | − | + |
| CHO-K1 | 23.6 ± 3.1 | 0.2 ± 0.016 | 15.1 ± 0.1 | 0.8 ± 0.05 | 6.7 ± 0.3 | 0.26 ± 0.08 |
| HEK-293 | 27.3 ± 0.8 | 0.2 ± 0.04 | 29.4 ± 1.6 | 1.9 ± 0.1 | 5.5 ± 0.4 | 0.2 ± 0.016 |
| HaCaT | 0.9 ± 0.03 | a) | 0.6 ± 0.1 | 0.5 ± 0.05 | 0.7 ± 0.07 | 0.5 ± 0.05 |
| fibroblasts[b] | 1.0 ± 0.04 | a) | 2.6 ± 0.1 | 0.2 ± 0.02 | 0.1 ± 0.01 | a) |
| keratinocytes[c] | 1.5 ± 0.05 | a) | 11.9 ± 1.3 | 0.3 ± 0.02 | 0.5 ± 0.01 | a) |

SEAP production was quantified 48 h after transient co-transfection of pMG10 ($P_{TtgR1}$-SEAP-pA) and either pMG11 ($P_{SV40}$-$TtgA_1$-pA; TtgR-VP16), pMG18 ($P_{SV40}$-$TtgA_2$-pA; TtgR-p65) or pMG19 ($P_{SV40}$-$TtgA_3$-pA; TtgR-E2F4).
[a]Undetectable
[b]human primary fibroblasts
[c]human primary keratinocytes The invention in particular relates to a vector comprising a TtgR-specific operator sequence ($O_{TtgR}$) located 5' of a minimal human cytomegalovirus immediate early promoter ($P_{hCMVmin}$), and a polynucleotide coding for an endogenous or, preferably, exogenous protein, and to such vector wherein $O_{TtgR}$ is directly linked to the 5' end of $P_{hCMVmin}$ or wherein between 1 and 20 base pairs, preferably 2, 4 or 10 base pairs, are inserted between $O_{TtgR}$ and the 5' end of $P_{hCMVmin}$.

Phloretin-Responsive Promoter Variants that Differ in the Distance Between $O_{TtgR}$ and Minimal Promoter.

The torsion angle and the distance between operator-bound transactivator and minimal promoter play central roles in the efficient assembly of the transcription-initiation machinery. With the goal of achieving the optimal design for $P_{TtgR}$ configurations linkers of 2 bp increments are engineered, ranging from 0 to 10 bp, between $O_{TtgR}$ and $P_{hCMVmin}$, and SEAP expression vectors generated, which are isogenic to pMG10 ($P_{TtgR1}$, pMG10, $O_{TtgR}$-0bp-$P_{hCMVmin}$; $P_{TtgR2}$, pMG20, $O_{TtgR}$-2bq-$P_{hCMVmin}$; $P_{TtgR3}$, pMG21, $O_{TtgR}$-4-bp-$P_{hCMVmin}$; $P_{TtgR4}$; pMG22, $O_{TtgR}$-6 bp-$P_{hCMVmin}$; $P_{TtgR5}$, pMG23, $O_{TtgR}$-8bp-$P_{hCMVmin}$; $P_{TtgR6}$, pMG24, $O_{TtgR}$-10bp-$P_{hCMVmin}$) (see Table 4 below). Each of the SEAP expression vectors harboring phloretin-responsive promoter variants are co-transfected with pMG11 ($P_{SV40}$-$TtgA_1$-pA), pMG18 ($P_{SV40}$-$TtgA_2$-pA) or pMG19 ($P_{SV40}$-$TtgA_3$-pA) into CHO-K1, and SEAP production is profiled after cultivation for 48 h in medium containing 0, 25 and 50 µM phloretin (FIG. 3A-C).

$P_{TtgR1}$ harboring 0 bp between $O_{Ttgr}$ and $P_{hCMVmin}$ drives maximum SEAP expression and shows the tightest repression. pMG20, pMG21 and pMG24, with increments of 2, 4 and 10 bp exhibit similar regulation performance. However, 6 and 8 bp increments (pMG22 and pMG23) has a strong negative effect on maximum transgene expression and repression. All promoter variants show similar TtgA-specific expression profiles indicating that performance of transactivators and promoters can independently be optimized (FIG. 3A-C).

Furthermore the invention relates to a vector comprising a polynucleotide coding for the TtgR protein fused to a transactivation domain, a polynucleotide coding for an endogenous or, preferably, exogenous protein, a TtgR-specific operator sequence ($O_{TtgR}$) and a promoter, in particular to a vector comprising promoter $P_{TtgR1}$, transactivator $TtgA_1$, and further the polioviral internal ribosome entry site ($IRES_{PV}$).

Autoregulated Phloretin-Inducible Transgene Expression.

In addition to the classical two-vector design (transactivator and responsive promoter encoded on separate plasmids) an autoregulated version of the synthetic phloretin control circuit is constructed, which enables simultaneous $P_{TtgR1}$-driven expression of the transactivator ($T_{tgA1}$) and the transgene (SEAP) in a single-vector format. Following transfection of pMG13 ($P_{TtgR1}$-SEAP-$IRES_{PV}$-$TtgA_1$-pA) in CHO-K1, leaky $P_{TtgR1}$-driven transcripts lead to cap-independent translation of initial $TtgA_1$, mediated by the polioviral internal ribosome entry site ($IRES_{PV}$), which triggers, in an autoregulated positive feedback loop, full expression of $TtgA_1$ along with co-cistronically encoded SEAP. In the presence of 50 µM phloretin the positive feedback loop is interrupted as $TtgA_1$ no longer binds $P_{TtgR1}$ and SEAP is completely repressed (FIG. 4).

Compatibility of PEACE Control with Other Transgene Regulation Circuits.

To evaluate the functional compatibility of PEACE with the established tetracycline— [$TET_{OFF}$; Gossen M., Bujard H., 1992, *Proc Natl Acad Sci USA* 89(12):5547-5551] and macrolide— [$E_{OFF}$; Weber W., et al., 2002, *Nat Biotechnol* 20(9):901-907] responsive expression circuits CHO-$PEACE_8$ is transiently transfected, transgenic for phloretin-responsive SEAP expression, with either the $TET_{OFF}$-(pSAM200, $P_{SV40}$-tTA-pA; pBP99, $P_{hCMV*-1}$-SAMY-pA) or the $E_{OFF}$-(PWW35, $P_{SV40}$-ET1-pA; pBP100, $P_{ETR3}$-SAMY-pA) system set to control the *Bacillus stearothermophilus*-derived secreted α-amylase (SAMY) in response to tetracycline and erythromycin, respectively. SEAP and SAMY expression are scored 48 h after cultivation of the transfected populations in the presence (50 µM; 2 µg/mL) or absence of the inducer molecules (phloretin, tetracycline, erythromycin). Analysis of cross-regulation shows no interference between PEACE, $TET_{OFF}$, and $E_{OFF}$ systems (Table 2 A and B).

TABLE 2

Compatibility of phloretin-, erythromycin- and tetracycline-responsive transgene control systems A: CHO-$PEACE_8$ transiently transfected with the tetracycline-responsive control system

| Inducer | −Tet/−Phl | −Tet/+Phl | +Tet/−Phl | +Tet/+Phl |
|---|---|---|---|---|
| Relative SEAP Production (%) | 100 ± 4.3 | 2.2 ± 0.2 | 93.2 ± 3.8 | 1.4 ± 0.2 |
| Relative SAMY Production (%) | 100 ± 5.2 | 98.1 ± 2.8 | 3.0 ± 0.4 | 4.0 ± 1.0 |

B: CHO-$PEACE_8$ transiently transfected with macrolide-responsive control system

| Inducer | −EM/−Phl | −EM/+Phl | +EM/−Phl | +EM/+Phl |
|---|---|---|---|---|
| Relative SEAP Production (%) | 100 ± 6.0 | 2.0 ± 1.2 | 102.7 ± 5.3 | 1.6 ± 0.9 |
| Relative SAMY Production (%) | 100 ± 5.2 | 100.6 ± 7.0 | 1.5 ± 1.8 | 1.7 ± 2.0 |

CHO-$PEACE_8$ were co-transfected with (A) pSAM200 ($P_{SV40}$-tTA-pA) and pBP99 ($P_{hCMV*-1}$-SAMY-pA) or (B) pWW35 ($P_{SV40}$-ET1-pA) and pBP100 ($P_{ETR3}$-SAMY-pA) and grown for 48 h in the presence and absence of phloretin (Phl, 50 µM), erythromycin (EM, 2 µg/mL) or tetracycline (Tet, 2 µg/mL) before SEAP and SAMY production was assessed.

Regulation Performance of Phloretin and Other Flavonoids and Chalcones.

Based on the fact that the TtgR protein of *P. putida* binds several plant-derived flavonoids and chalcones with high affinity (Teran W. et al., loc. cit.), their PEACE-controlling capacities in mammalian cells has been utilised. CHO-K1 are transiently (co-)transfected with either pMG10 ($P_{TtgR1}$-SEAP-pA) and pMG11 ($P_{SV40}$-$TtgA_1$-pA), to score regulation performance, or with pSEAP2-Control ($P_{SV40}$-SEAP-pA), to assess compound-related cytotoxicity, and then cultivated for 48 h in medium containing different concentrations (0, 25, 50 µM) of specific flavonoid type compounds (berberine, butylparaben, genistein, luteolin, β-naphthol, naringenin, phloretin, phloridzin or quercetin) before SEAP production is profiled (FIG. 5A). Whereas genistein, luteolin, β-naphthol, naringenin and quercetine are cytotoxic within the tested concentration range (genistein only at 50 µM), berberine, butylparaben, phloridzin and phloretin do not reduce cell viability. However, berberine fails to control PEACE and butylparaben as well as phloridzin are able to regulate but not fully repress SEAP production (FIG. 5B). Therefore, phloretin which enables maximum expression levels as well as full transgene repression is the preferred PEACE inducer.

The invention further relates to a mammalian cell comprising the mentioned vectors, either stably or transiently transfected with the described vectors, and to such mammalian cells in a nanocontainer or microcontainer, e.g. in encapsulated form. A nanocontainer may be a virus, preferably an attenuated virus, in particular a viral capsid, synthetic or semi-synthetic nano- or microparticles, such as spheres or tubes of a suitable geometry to incorporate mammalian cells, and the nano- or microcontainers formed in situ by encapsulation of mammalian cells, for example with alginate-poly-L-lysine. A particular example of a suitable nano- or microcontainer is the hollow fibre manufactured under the trade name CELLMAX®. The invention further relates to a mammal excluding man comprising a mammalian cell as described, in particular a mammalian cell in a nano- or microcontainer.

Phloretin-Controlled Transgene Expression is Functional in Different Mammalian Cell Lines and Human Primary Cells.

To demonstrate its versatility PEACE is tested in several immortalized mammalian cell lines as well as in human primary cells. pMG10 ($P_{TtgR1}$-SEAP-pA) and pMG11 ($P_{SV40}$-$TtgA_1$-pA) are co-transfected into BHK-21, COS-7, HaCaT, HEK-293, HT-1080 and NIH/3T3 cell lines as well as into primary human fibroblasts and keratinocytes, and cultivated for 48 h in the presence (50 μM) and absence of phloretin, followed by scoring of SEAP levels (Table 3). PEACE-controlled transgene expression is functional in all tested cell lines indicating that this technology will be broadly applicable.

TABLE 3

PEACE-controlled transgene expression in different mammalian cells

| Cell Line | 0 μM Phloretin | 50 μM Phloretin |
|---|---|---|
| BHK-21 | 14.4 ± 0.4 U/L | 1.5 ± 0.2 U/L |
| COS-7 | 1.3 ± 0.02 U/L | * |
| HaCaT | 0.9 ± 0.03 U/L | * |
| HEK-293 | 27.3 ± 0.8 U/L | 0.2 ± 0.04 U/L |
| HT-1080 | 7.8 ± 0.2 U/L | * |
| NIH/3T3 | 8.5 ± 0.3 U/L | * |
| Primary human fibroblasts | 1.0 ± 0.04 U/L | * |
| Primary human keratinocytes | 1.5 ± 0.05 U/L | * |

SEAP production was quantified 48 h after co-transfection pMG10 ($P_{TtgR1}$-SEAP-pA) and pMG11 ($P_{SV40}$-TtgA$_1$-pA) into indicated cell lines and primary cells.
*Undetectable Expression Kinetics, Adjustability and Reversibility of PEACE-Controlled Transgene Expression in a Stable Transgenic CHO-K1 Cell Line.

By sequential transfection and clonal selection of pMG11 and pMG10 into CHO-K1 5 double-transgenic cell lines (CHO-PEACE) are generated, all of which show phloretin-regulated SEAP expression but differ in their overall regulation performance (maximum and leaky expression levels; FIG. 6). CHO-PEACE$_8$, which is the preferred cell line, shows (i) unchanged maximum SEAP expression levels in long-term cultures over 60 days (day 0, 70.9±3.1 U/L; day 60, 67.6±2.7 U/L), (ii) excellent adjustability (FIG. 7A), (iii) exponential SEAP expression kinetics (FIG. 7B), (iv) full reversibility of transgene expression (FIG. 7C) and (v) optimal compatibility with other transgene regulation circuits (Table 2).

Time-Delayed Induction of Product Gene Expression in a Prototype Biopharmaceutical Manufacturing Scenario.

Since phloretin is a non-toxic fruit component, it is an ideal product gene inducer for biopharmaceutical manufacturing scenarios, which require precise timing or dosing of difficult-to-express protein pharmaceuticals. Also, since phloretin has a determined half-live of 70 h in mammalian cell culture systems any production culture can be programmed to start product gene expression at a predefined point in time as phloretin concentrations drop below a repressing threshold level. A 1 L BioWave® bioreactor is inoculated with 2×10$^3$ CHO-PEACE$_8$ and different transgene-repressing phloretin doses of 60, 80 or 100 μM. While CHO-PEACE$_8$ grows exponentially from the start of the bioprocess, SEAP production gradually increases once phloretin is degraded to non-repressive levels (40 μM; FIG. 8). Using PEACE mammalian production cultures can indeed be programmed for timely induction of product gene expression without any process intervention.

Phloretin-Mediated Transdermal Gene Expression in Subcutaneous Implants in Mice.

Since phloretin is suggested as a penetration enhancer for transdermal drug delivery and is shown to propagate systemically in rodents following local skin-based administration (Auner B. G. et al., loc. cit.), phloretin has been evaluated as a potential transdermal therapeutic transgene expression inducer. CHO-PEACE$_8$ is microencapsulated in coherent alginate-PLL-alginate capsules and implanted subcutaneously into mice. The back of treated mice is partially shaved and vaseline-based skin lotions (200 μL) containing different amounts of phloretin (0-42 mg) are put on every day. The SEAP levels detected in treated mice 72 h after implantation shows phloretin-dependent dose-response characteristics akin to the ones observed with the same microencapsulated implant batch cultivated and exposed to phloretin in vitro (FIGS. 9A and 8). Control mice receiving CHO-K1 cells transgenic for constitutive SEAP expression are insensitive to any treatment with phloretin-containing skin lotion (0 mg phloretin: 6.2±0.43 U/L; 42 mg phloretin: 6.02±0.58 U/L).

The invention further relates to a vector comprising the genetic code for *Pseudomonas putida* DOT-T1E-derived bacterial repressor TtgR fused to a transrepressor domain, in particular to such a vector comprising the genetic code for TtgR and the krab transrepression domain of human Kruppel-associated box-protein and the constitutive simian virus 40 promoter ($P_{SV40}$) such that the transrepressor TtgK resulting from the fusion of the proteins TtgR with KRAB is under control of $P_{SV40}$. Other transrepressor domains considered are domains derived from or related to, for example, the v-erbA oncogenes product, the thyroid hormone receptor, the Ssn6/Tup1 protein complex, the SIRI protein, NeP1, TSF3, SF1, WT1, Oct-2.1, E4BP4, and ZF5, and also those listed in U.S. Pat. No. 6,287,813. Likewise the invention relates to a vector comprising TtgR protein fused to a transrepressor domain, a polynucleotide coding for an exogenous protein, a TtgR-specific operator sequence ($O_{TtgR}$) and a promoter.

Design of the PEACE-System for Positive Regulation (PEACE-ON).

By fusing TtgR to the human Kruppel-associated box-protein (KRAB) (Moosmann P., Georgiev O., Thiesen H. J., Hagmann M., Schaffner W., 1977, *Biol Chem* 378(7):669-677) a synthetic mammalian transrepressor (TtgK) is created, which is able to bind and inhibit transcription from a promoter ($P_{TtgR}$ON) harboring eight $O_{TtgR}$-elements located 3' of a constitutive simian virus 40 promoter ($P_{SV40}$), in a phloretin-responsive manner (FIGS. 10A and B). Co-transfection of the constitutive TtgK expression vector pMG28 ($P_{SV40}$-TtgK-pA) and pMG27 ($P_{TtgR}$ON-SEAP-pA) encoding a TtgK-specific $P_{TtgR}$ON-driven SEAP expression unit, results in low-level, basal SEAP expression (2.3±0.26 U/L). Addition of increasing concentrations of phloretin (0-50 μM) to a culture of pMG27- and pMG28-co-transfected CHO-K1 cells resulted in dose-dependent induction of SEAP expression (FIG. 10C). These data indicate that PEACE-controlled transgene expression can either be repressed by the addition of phloretin (see PEACE-system FIG. 2A-C), or induced as shown in the PEACE-ON setup (FIG. 10A-C). In order to reduce basal expression (leakiness) of the system, coupled transcriptional and translational strategies for reducing leakiness can be employed: (i) Deployment of different constitutive promoters; (ii) variation of the number of operator sequences ($O_{TtgR}$) in 3' orientation of the promoter (1-12 $O_{TtgR}$-repeats) and/or addition of operator sequences in 5' orientation of the constitutive promoter (1-12 $O_{TtgR}$-repeats); (iii) mediated knock-down of specifically tagged genes of interest (goi) via cistronic siRNA.

EXAMPLES

Expression Vector Design.

pMG10 ($P_{TtgR1}$-SEAP-pA) harbors a phloretin-reponsive SEAP expression unit, and pMG11 ($P_{SV40}$-TtgA$_1$-pA) encodes constitutive expression of the phloretin-dependent transactivator. Detailed information on expression vector design and plasmids used is provided in the following Table 4.

TABLE 4

Expression vectors and oligonucleotides

| Plasmid | Description | Ref |
|---|---|---|
| pBP10 | Vector encoding a $P_{ETR5}$-driven SEAP expression unit ($P_{ETR5}$-SEAP-pA; $P_{ETR5}$, ETR-2bp-$P_{hCMVmin}$) | (a) |
| pBP11 | Vector encoding a $P_{ETR6}$-driven SEAP expression unit ($P_{ETR6}$-SEAP-pA; $P_{ETR6}$, ETR-4bp-$P_{hCMVmin}$) | (a) |
| pBP12 | Vector encoding a $P_{ETR7}$-driven SEAP expression unit ($P_{ETR7}$-SEAP-pA; $P_{ETR7}$, ETR-6bp-$P_{hCMVmin}$) | (a) |
| pBP13 | Vector encoding a $P_{ETR8}$-driven SEAP expression unit ($P_{ETR8}$-SEAP-pA; $P_{ETR8}$, ETR-8bp-$P_{hCMVmin}$) | (a) |
| pBP14 | Vector encoding a $P_{ETR9}$-driven SEAP expression unit ($P_{ETR9}$-SEAP-pA; $P_{ETR9}$, ETR-10bp-$P_{hCMVmin}$) | (a) |
| pBP99 | Vector encoding a tetracycline-responsive SAMY expression unit ($P_{hCMV*-1}$-SAMY-pA). pCF59 was restricted with BprPI/EcoRV and religated. | |
| pBP100 | Vector encoding an erythromycin-responsive SAMY expression unit ($P_{ETR3}$-SAMY-pA) | (b) |
| pCF59 | Vector encoding $P_{PIR}$-driven SAMY expression ($P_{hCMV*-1}$-pA-IRES-$P_{PIR}$-SAMY-pA). SAMY was excised from pSS158 using SpeI/BglII and ligated into pMF187 (SpeI/BglII). | |
| pMF111 | Vector encoding a $P_{hCMV*-1}$-driven SEAP expression unit ($P_{hCMV*-1}$-SEAP-pA) | (c) |
| pMF187 | Dual-regulated expression vector ($P_{hCMV*-1}$-MCSI-IRES-MCSII-pA$_I$-$P_{PIR}$-MCSIII-pA$_{II}$) | (d) |
| pMG9 | Vector encoding $O_{TtgR}$-0bp-$P_{hCMVmin}$-ET1-pA, $O_{TtgR}$-0bp-$P_{hCMVmin}$ was PCR-amplified from pRevTRE using OMG21: 5'-gatcaagctt*gacgtc* CAGTATTTACAAACAACCATGAATGTAAGTATATTC*cctgcagg*TCG AGCTCGGTACCCGGGTC-3' (SEQ ID NO: 1) and OWW22: 5'-gcta *gaattc*CGCGGAGGCTGGATCGG-3' (SEQ ID NO: 2) (upper case, annealing sequence; lower case italics, restriction sites; upper case italics, $O_{TtgR}$), digested with AatII/EcoRI and ligated into pWW35 (AatII/EcoRI). | |
| pMG10 | Vector encoding a $P_{TtgR1}$-driven SEAP expression unit ($P_{TtgR1}$-SEAP-pA; $P_{TtgR1}$, $O_{TtgR}$-0bp-$P_{hCMVmin}$). $O_{TtgR}$-0bp-$P_{hCMVmin}$ was excised from pMG9 (SspI/EcoRI) and ligated into pMF111 (SspI/EcoRI). | |
| pMG11 | Constitutive TtgA$_1$ expression vector ($P_{SV40}$-TtgA$_1$-pA). TtgR was excised from pUC19-TtgR (EcoRI/BssHII) and ligated into pWW35 (EcoRI/BssHII). | |
| pMG13 | Autoregulated phloretin-controlled SEAP expression vector ($P_{TtgR1}$-SEAP-IRES$_{PV}$-TtgA$_1$-pA). TtgA$_1$ was excised from pMG11 (SspI/NotI) and ligated into pMG10 (SspI/NotI). | |
| pMG18 | Constitutive TtgA$_2$ expression vector ($P_{SV40}$-TtgA$_2$-pA). p65 was excised from pWW42 (BssHII/BamHI) and ligated into pMG11 (BssHII/BamHI). | |
| pMG19 | Constitutive TtgA$_3$ expression vector ($P_{SV40}$-TtgA$_3$-pA). The E2F4 transactivation domain was excised from pWW64 (BssHII/BamHI) and ligated into pMG11 (BssHII/BamHI). | |
| pMG20 | Vector encoding a $P_{TtgR2}$-driven SEAP expression unit ($P_{TtgR2}$-SEAP-pA; $P_{TtgR2}$, $O_{TtgR}$-2bp-$P_{hCMVmin}$). 2bp-$P_{hCMVmin}$-SEAP was excised from pBP10 (SspI/EcoRI) and ligated into pMG10 (SspI/EcoRI). | |
| pMG21 | Vector encoding a $P_{TtgR3}$-driven SEAP expression unit ($P_{TtgR3}$-SEAP-pA; $P_{TtgR3}$, $O_{TtgR}$-4bp-$P_{hCMVmin}$). 4bp-$P_{hCMVmin}$-SEAP was excised from pBP11 (SspI/EcoRI) and ligated into pMG10 (SspI/EcoRI). | |
| pMG22 | Vector encoding a $P_{TtgR4}$-driven SEAP expression unit ($P_{TtgR4}$-SEAP-pA; $P_{TtgR4}$, $O_{TtgR}$-6bp-$P_{hCMVmin}$). 6bp-$P_{hCMVmin}$-SEAP was excised from pBP12 (SspI/EcoRI) and ligated into pMG10 (SspI/EcoRI). | |
| pMG23 | Vector encoding a $P_{TtgR5}$-driven SEAP expression unit ($P_{TtgR5}$-SEAP-pA; $P_{TtgR5}$, $O_{TtgR}$-8bp-$P_{hCMVmin}$). 8bp-$P_{hCMVmin}$-SEAP was excised from pBP13 (SspI/EcoRI) and ligated into pMG10 (SspI/EcoRI). | |
| pMG24 | Vector encoding a $P_{TtgR6}$-driven expression unit ($P_{TtgR6}$-SEAP-pA; $P_{TtgR6}$, $O_{TtgR}$-10bp-$P_{hCMVmin}$). 10bp-$P_{hCMVmin}$-SEAP was excised from pBP14 (SspI/EcoRI) and ligated into pMG10 (SspI/EcoRI). | |
| pPur | Selection vector conferring puromycin resistance | (e) |
| pRevTRE | Oncoretroviral expression vector containing a tetracycline-responsive expression unit | (e) |
| PSAM200 | Constitutive tTA expression vector ($P_{SV40}$-tTA-pA) | (c) |
| pSEAP2-Control | Constitutive SEAP expression vector ($P_{SV40}$-SEAP-pA) | (e) |
| pSS158 | $P_{hCMV}$-driven SAMY expression vector ($P_{hCMV}$-SAMY-pA) | (f) |
| pSV2neo | Selection vector conferring neomycin resistance | (e) |
| pUC19-TtgR | Cloning vector containing the TtgR (EcoRI-TtgR-BssHII) | (g) |
| pWW35 | Constitutive ET1 expression vector ($P_{SV40}$-ET1-pA) | (b) |

TABLE 4-continued

Expression vectors and oligonucleotides

| Plasmid | Description | Ref |
|---|---|---|
| pWW42 | Constitutive ET2 expression vector ($P_{SV40}$-ET2-pA) | (b) |
| pWW64 | Constitutive ET3 expression vector ($P_{SV40}$-ET3-pA) | (a) |

References:
(a) Weber W., Kramer B. P., Fux C., Keller B., Fussenegger M., 2002, *J Gene Med* 4(6): 676-686.
(b) Weber W., et al., 2002, *Nat Biotechnol* 20(9): 901-907.
(c) Fussenegger M., Moser S., Mazur X., Bailey J. E., 1997, *Biotechnol Prog* 13(6): 733-740.
(d) Moser S., et al., 2001, *J Gene Med* 3(6): 529-549.
(e) Clontech, Palo Alto, CA, USA.
(f) Schlatter S., Rimann M., Kelm J., Fussenegger M., 2002, *Gene* 282(1-2): 19-31.
(g) Picoscript, Houston, TX, USA.

Abbreviations:
E2F4, transactivation domain of the human E2F transcription factor 4;
ET1, macrolide-dependent transactivator (E-VP16);
ET2, macrolide-dependent transactivator (E-p65);
ET3, macrolide-dependent transactivator (E-E2F4);
ETR, operator specific for macrolide-dependent transactivators;
$IRES_{PV}$, polioviral internal ribosome entry site;
NF-κB, human transcription factor;
$O_{TtgR}$, TtgR-specific operator;
p65, transactivation domain of NF-κB;
pA, polyadenylation site;
$P_{ETR3-9}$, macrolide-responsive promoters containing different spacers between ETR and $P_{hCMVmin}$;
$P_{hCMV}$, human cytomegalovirus immediate early promoter;
$P_{hCMVmin}$, minimal $P_{hCMV}$;
$P_{hCMV*-1}$, tetracycline-responsive promoter;
$P_{PIR3}$, streptogramin-responsive promoter;
$P_{SV40}$, simian virus 40 promoter;
$P_{TtgR1-6}$, phloretin-responsive promoters containing different spacers between $O_{TtgR}$ and $P_{hCMVmin}$;
SEAP, human placental secreted alkaline phosphatase;
SAMY, *Bacillus stearothermophilus*-derived secreted α-amylase;
TtgR, repressor of the *Pseudomonas putida* DOT-T1E ABC multi-drug efflux pump;
$TtgA_1$, phloretin dependant transactivator (TtgR-VP16);
$TtgA_2$, phloretin dependant transactivator (TtgR-p65);
$TtgA_3$, phloretin dependant transactivator (TtgR-E2F4);
VP16, Herpes simplex virus-derived transactivation domain.

Cell Culture and Transfection.

Wild-type Chinese hamster ovary cells (CHO-K1, ATCC: CCL-61) and their derivatives are cultivated in standard medium: ChoMaster® HTS (Cell Culture Technologies, Gravesano, Switzerland) supplemented with 5% (v/v) fetal calf serum (FCS, PAN Biotech GmbH, Aidenbach, Germany, Cat. No. 3302, Lot No. P251110) and 1% (v/v) penicillin/streptomycin solution (Sigma, St Louis, Mo., USA, Cat. No. P4458). Human embryonic kidney cells (HEK-293, Mitta B., et al., 2002, Nucleic Acids Res 30(21):e113), African green monkey kidney cells (COS-7, ATCC: CRL-1651), baby hamster kidney cells (BHK-21, ATCC: CCL10), human fibrosarcoma cells (HT-1080, ATCC: CCL-121), the human keratinocyte cell line HaCaT (Boukamp P., et al., 1988, *J Cell Biol* 106(3):761-771) and mouse fibroblasts (NIH/3T3, ATCC: CRL-1658) are cultured in Dulbecco's modified Eagle's medium (DMEM; Invitrogen, Cat. No. 52100-39) supplemented with 10% FCS (v/v) and 1% (v/v) penicillin/streptomycin solution. Primary human foreskin fibroblasts are cultivated in DMEM supplemented with 20% FCS (v/v) and 1% (v/v) penicillin/streptomycin solution and primary human foreskin keratinocytes are cultured in chemically defined serum-free keratinocyte medium (Invitrogen, Cat. No. 10744019). All cell types are cultivated at 37° C. in a 5% $CO_2$-containing humidified atmosphere. For transient transfection of CHO-K1, 1 µg of total plasmid DNA (for co-transfection an equal amount of each plasmid) is transfected into 50,000 cells per well of a 24-well plate according to an optimized calcium phosphate protocol (Greber D., Fussenegger M., 2007, *Biotechnol Bioeng* 96(5):821-834). Plasmid DNA is diluted to a total volume of 25 µL 0.5 M $CaCl_2$ solution, which is mixed with 25 µL 2×HBS solution (50 mM HEPES, 280 mM NaCl, 1.5 mM $Na_2HPO_4$, pH 7.1). After incubation for 15 min at room temperature, the precipitates are immediately added to the well and centrifuged onto the cells (5 min at 1,200×g) to increase transfection efficiency. After 3 h, the cells are treated with 0.5 mL glycerol solution (ChoMaster® HTS medium containing 15% glycerol) for 60 sec. After washing once with phosphate-buffered saline (PBS, Dulbecco's Phosphate-Buffered Saline; Invitrogen, Cat. No. 21600-0069), cells are cultivated in 0.5 mL standard ChoMaster® HTS medium in the presence or absence of different concentrations of phloretin. For transfection of BHK-21, COS-7 and HEK-293, plasmid DNA-$Ca_2PO_4$ precipitate is prepared and applied to the cells as described above. HEK-293 and COS-7 cells are washed once with PBS after 3 h incubation with the DNA-$Ca_2PO_4$ precipitate and subsequently cultivated in standard DMEM, while BHK-21 cells are incubated overnight with the precipitates and then cultivated in DMEM medium after being washed once with PBS. HaCaT, HT-1080, NIH/3T3 as well as primary human fibroblasts and keratinocytes are transfected with Fugene™ 6 (Roche Diagnostics AG, Basel, Switzerland, Cat. No. 11814443001) according to the manufacturer's protocol and cultivated in the cell culture medium specified above. After transfection, all cells are cultivated in DMEM supplemented with different concentrations of phloretin and reporter protein levels are profiled 48 h after transfection, unless otherwise indicated.

Construction of Stable Cell Lines.

The stable CHO-$PEACE_8$ cell line, transgenic for phloretin-controlled SEAP expression, is constructed in two steps:

(i) CHO-K1 cells are co-transfected with pMG11 ($P_{SV40}$-TtgA$_1$-pA) and pSV2neo (Clontech, Cat. No. 6172-1) at a ratio of 20:1 and clonal selection results in the cell line CHO-TtgA. (ii) CHO-TtgA is co-transfected with pMG10 ($P_{TtgR1}$-SEAP-pA) and pPur (Clontech, Cat. No. 6156-1) (ratio of 20:1) and the phloretin-responsive SEAP-producing double-transgenic cell line CHO-PEACE$_8$ is chosen after clonal selection. Phloretin-dependent dose-response characteristics of CHO-PEACE$_8$ are analyzed by culturing 100,000 cells/mL for 48 h in standard ChoMaster® HTS medium at different phloretin concentrations ranging from 0 to 70 µM. Reversibility of phloretin-mediated SEAP production is assessed by cultivating CHO-PEACE$_8$ (100,000 cells/mL) for 144 h while alternating phloretin concentrations from 0 to 50 µM every 48 h.

Quantification of Reporter Protein Production.

Production of the human placental secreted alkaline phosphatase (SEAP) is quantified using a p-nitrophenylphosphate-based light absorbance time course. *Bacillus stearothermophilus*-derived secreted α-amylase (SAMY) levels are assessed using the blue starch Phadebas® assay (Pharmacia Upjohn, Peapack, N.J., USA; Cat. No. 10-5380-32) (Schlatter S., Rimann M., Kelm J., Fussenegger M., 2002, *Gene* 282(1-2):19-31).

In Vivo Methods.

CHO-PEACE$_8$ and CHO-SEAP$_{18}$ (Fluri D. A., Kemmer C., Daoud-El Baba M., Fussenegger M., 2008, *J Control Release* 131(3):211-219) are encapsulated in alginate-poly-(L-lysine)-alginate beads (400 µm; 200 cells/capsule) using an Inotech Encapsulator Research IE-50R (Recipharm, Basel, Switzerland) according to the manufacturer's instructions and the following parameters: 0.2 mm nozzle, 20 mL syringe at a flow rate of 405 units, nozzle vibration frequency of 1024 Hz and 900 V for bead dispersion. The back of female OF1 mice (oncins France souche 1, Charles River Laboratories, France) is shaved and 300 µL of ChoMaster® HTS containing 2×10$^6$ encapsulated CHO-PEACE$_8$ are subcutaneously injected. Control mice are injected with microencapsulated CHO-K1. Shaving ensures direct contact of the phloretin-containing cream with the skin of the animal. One hour after implantation 200 µL of the phloretin-containing cream is applied to the skin around the injection site. The phloretin amounts in creams ranges from 0 to 42 mg. The cream is applied once a day for up to three days. Thereafter, the mice are sacrificed, blood samples collected and SEAP levels are quantified in the serum which is isolated using microtainer SST tube according to the manufacturer's instructions (Beckton Dickinson, Plymouth, UK). All the experiments involving mice are performed according to the directives of the European Community Council (86/609/EEC).

Bioreactor Operation.

CHO-PEACE$_8$ (inoculum of 2×10$^3$ cells/mL) are cultivated in a BioWave 20SPS-F bioreactor (Wave Biotech AG, Tagelswangen, Switzerland) equipped with a 2 L Wave Bag® optimized for optical pH and DO control of the 1 L culture. The bioreactor is operated at a rocking rate of 15 min$^{-1}$, a rocking angle of 6° and an aeration rate of 100 mL/min with inlet gas humidification (HumiCare® 200, Gruendler Medical, Freudenstadt, Germany) to prevent evaporation of the medium. The medium (ChoMaster® HTS, 5% FCS, 1% penicillin/streptomycin) is supplemented with 60, 80 or 100 µM phloretin.

Inducer Compounds and Formulation of the Skin Lotion.

Berberine (Acros, Geel, Belgium, Cat. No. 20425-0100) and luteolin (Alfa Aesar, Karlsruhe, Germany, Cat. No. L14186) are prepared as 10 mM stock solutions in 1:5 (v/v) DMSO/H$_2$O. Butylparaben (ABCR, Karlsruhe, Germany, Cat. No. AV14043), genistein (Axonlab, Baden, Switzerland, Cat. No. A2202.0050), β-naphthol (Sigma, Cat. No. 185507), naringenin (Sigma, Cat. No. N5893), phloretin (Sigma, Cat. No. P7912), phloridzin (Sigma, Cat. No. P3449) and quercetin (Sigma, Cat. No. Q0125) are prepared as 50 mM stock solution in DMSO and are used at a final concentration of 50 µM unless indicated otherwise. The vaseline-based phloretin-containing creams are professionally formulated (Pharmacy Hoengg Ltd., Zurich, Switzerland) and contain 25, 12.5, 6.25 and 3.125% (wt/wt) of phloretin. 200 µl skin lotion are topically applied per mouse and treatment, which corresponds to a respective total phloretin amount per dose of 42, 21, 10.5 and 5.25 mg. Tetracycline (Sigma, Cat. No. T7660) is prepared as a 1 mg/mL stock solution in H$_2$O, and erythromycin (Fluka, Buchs, Switzerland, Cat. No. 45673) as a stock solution of 1 mg/mL in ethanol. Both antibiotics are used at a final concentration of 2 µg/mL.

In order to quantify phloretin in cell culture medium, the samples are added to 5×10$^4$ CHO-PEACE$_8$ and incubated for 48 h prior to SEAP quantification. Phloretin levels are calculated by comparing SEAP production with a calibration curve (FIG. 7A), established using the same parameters and defined phloretin concentrations. Similarly, the half-live of phloretin is estimated based on the degradation dynamics observed in cell culture.

The invention claimed is:

1. An in vitro method for controlling transgene expression, the method comprising:
  (i) transfecting isolated mammalian cells with a first vector comprising a polynucleotide sequence operably linked to a constitutively active promoter sequence, wherein said polynucleotide sequence encoding a fusion protein consisting of a *Pseudomonas putida* DOT-T1E-derived bacterial repressor protein TtgR and a transactivation domain, or a fusion protein consisting of TtgR and a transrepressor domain; and
  transfecting said isolated mammalian cells with a second vector comprising a TtgR-specific operator ($O_{TtgR}$) sequence operably linked to a promoter sequence, wherein said promoter sequence is operably linked to a polynucleotide sequence encoding an endogenous or exogenous protein; wherein expression of TtgR-transactivation domain fusion protein in said cells induces expression of said endogenous or exogenous protein; or wherein expression of TtgR-transrepressor domain fusion protein in said cells inhibits expression of said endogenous or exogenous protein;
  or
  transfecting isolated mammalian cells with a single vector comprising a first polynucleotide sequence operably linked to a constitutively active promoter sequence, wherein said polynucleotide sequence encoding a fusion protein consisting of a TtgR and a transactivation domain, or a fusion protein consisting of a TtgR and a transrepressor domain; and a second polynucleotide sequence comprising an $O_{TtgR}$ sequence operably linked to a promoter sequence, wherein said promoter sequence is operably linked to a polynucleotide sequence encoding an endogenous or exogenous protein; wherein expression of TtgR-transactivation domain fusion protein in said cells induces expression of said endogenous or exogenous protein; or wherein expression of TtgR-transrepressor domain fusion protein in said cells inhibits expression of said endogenous or exogenous protein; and
  (ii) contacting said cells with a non-toxic micromolar concentration range of a skin permeating compound selected from phloretin and butylparaben, wherein said skin permeating compound dissociates TtgR-transactivation domain fusion protein from $O_{TtgR}$ and results in repression of said protein expression; or wherein said skin permeating compound dissociates TtgR-transrepressor domain fusion protein from $O_{TtgR}$ and results in enhancement of said protein expression.

2. The method according to claim 1 wherein the skin permeating compound is butylparaben.

3. The method according to claim 1 wherein the skin permeating compound is phloretin.

4. An in vivo method for controlling transgene expression, the method comprising:

(i) transfecting isolated mammalian cells with a first vector comprising a polynucleotide sequence operably linked to a constitutively active promoter sequence, wherein said polynucleotide sequence encoding a fusion protein consisting of a *Pseudomonas putida* DOT-T1E-derived bacterial repressor protein TtgR and a transactivation domain, or a fusion protein consisting of TtgR and a transrepressor domain; and
  transfecting said isolated mammalian cells with a second vector comprising a TtgR-specific operator ($O_{TtgR}$) sequence operably linked to a promoter sequence, wherein said promoter sequence is operably linked to a polynucleotide sequence encoding an endogenous or exogenous protein; wherein expression of TtgR-transactivation domain fusion protein in said cells induces expression of said endogenous or exogenous protein; wherein expression of TtgR-transrepressor domain fusion protein in said cells inhibits expression of said endogenous or exogenous protein;
  or
  transfecting isolated mammalian cells with a single vector comprising a first polynucleotide sequence operably linked to a constitutively active promoter sequence, wherein said polynucleotide sequence encoding a fusion protein consisting of a TtgR and a transactivation domain, or a fusion protein consisting of a TtgR and a transrepressor domain; and a second polynucleotide sequence comprising an $O_{TtgR}$ sequence operably linked to a promoter sequence, wherein said promoter sequence is operably linked to a polynucleotide sequence encoding an endogenous or exogenous protein; wherein expression of TtgR-transactivation domain fusion protein in said cells induces expression of said endogenous or exogenous protein; wherein expression of TtgR-transrepressor domain fusion protein in said cells inhibits expression of said endogenous or exogenous protein;
  (ii) implanting said transfected cells into a mammal of the same species as the transfected cells by subcutaneous injection; and
  (iii) applying a skin permeating compound selected from phloretin and butylparaben to skin around the injection site of said cells in said mammal; wherein said skin permeating compound dissociates TtgR-transactivation domain fusion protein from $O_{TtgR}$ and results in repression of said protein expression in the transplanted cell; or wherein said skin permeating compound dissociates TtgR-transrepressor domain fusion protein from $O_{TtgR}$ and results in enhancement of said protein expression in the transplanted cell.

5. The method according to claim 4 wherein the skin permeating compound is butylparaben.

6. The method according to claim 4 wherein the skin permeating compound is phloretin.

* * * * *

SEQUENCE LISTING

```
<160> NUMBER OF SEQ ID NOS: 2

<210> SEQ ID NO 1
<211> LENGTH: 80
<212> TYPE: DNA
<213> ORGANISM: Artificial
<220> FEATURE:
<223> OTHER INFORMATION: Synthetic construct, primer for pRevTRE

<400> SEQUENCE: 1
gatcaagctt gacgtccagt atttacaaac aaccatgaat gtaagtatat tccctgcagg       60
tcgagctcgg tacccgggtc                                                   80

<210> SEQ ID NO 2
<211> LENGTH: 27
<212> TYPE: DNA
```

```
<213> ORGANISM: Artificial
<220> FEATURE:
<223> OTHER INFORMATION: Synthetic construct, primer for pRevTRE

<400> SEQUENCE: 2
gctagaattc cgcggaggct ggatcgg                                              27
```